United States Patent
Kusters et al.

(10) Patent No.: US 11,484,891 B2
(45) Date of Patent: Nov. 1, 2022

(54) ADJUSTMENT OF TARGET INTERFACE LOCATION BETWEEN SEPARATED FLUID COMPONENTS IN A CENTRIFUGE

(71) Applicant: Fenwal, Inc., Lake Zurich, IL (US)

(72) Inventors: Benjamin E. Kusters, Pleasant Prairie, WI (US); Richard I. Brown, Northbrook, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 345 days.

(21) Appl. No.: 16/878,650

(22) Filed: May 20, 2020

(65) Prior Publication Data
US 2020/0368763 A1   Nov. 26, 2020

Related U.S. Application Data

(60) Provisional application No. 62/851,712, filed on May 23, 2019.

(51) Int. Cl.
*G01N 33/28* (2006.01)
*B04B 11/02* (2006.01)
(Continued)

(52) U.S. Cl.
CPC ............ *B04B 11/02* (2013.01); *B04B 5/0442* (2013.01); *A61M 1/3693* (2013.01);
(Continued)

(58) Field of Classification Search
CPC . B04B 11/02; B04B 5/0442; B04B 2013/006; B04B 13/00; A61M 1/3693;
(Continued)

(56) References Cited

U.S. PATENT DOCUMENTS

| 5,194,145 A | 3/1993 | Schoendorfer |
| 5,316,667 A | 5/1994 | Brown et al. |

(Continued)

FOREIGN PATENT DOCUMENTS

| EP | 1946784 B1 | 10/2012 |
| WO | WO99/03557 A1 | 1/1999 |

(Continued)

OTHER PUBLICATIONS

Martina Meinke, Gerhard Müller, Ingo Gersonde and Moritz Friebel, "Determination Of Oxygen Saturation And Hematocrit Of Flowing Human Blood Using Two Different Spectrally Resolving Sensors", Biomed Tech 2006; 51:347-354 © 2006 by Walter de Gruyter—Berlin—New York. DOI 10.1515/BMT.2006.068.

(Continued)

*Primary Examiner* — Md M Rahman
(74) *Attorney, Agent, or Firm* — Cook Alex Ltd.

(57) ABSTRACT

A fluid separation device includes a centrifuge in which a fluid is separated into at least two components, with an interface therebetween. At least a portion of one of the separated fluid components is removed from the centrifuge and flows through a vessel. Light is reflected off of the separated fluid component in the vessel and received and analyzed to determine its main wavelength. If the main wavelength is higher than a maximum value, a target location of the interface is changed. If the main wavelength is less than the maximum value, then the location of the interface is compared to the target location. When the interface is sufficiently close to the target location, the optical density of the separated fluid component in the vessel is compared to a minimum value. If the optical density is less than the minimum value, the target location of the interface is changed.

20 Claims, 17 Drawing Sheets

(51) Int. Cl.
*B04B 5/04* (2006.01)
*A61M 1/36* (2006.01)
*B04B 13/00* (2006.01)

(52) U.S. Cl.
CPC . *A61M 2202/0415* (2013.01); *A61M 2230/30* (2013.01); *B04B 2013/006* (2013.01)

(58) Field of Classification Search
CPC ...... A61M 2202/0415; A61M 2230/30; A61M 1/265; A61M 2205/331; A61M 2205/3313; A61M 1/3696
USPC .......................................................... 356/70
See application file for complete search history.

(56) References Cited

U.S. PATENT DOCUMENTS

| | | | |
|---|---|---|---|
| 5,462,416 A | 10/1995 | Dennehey et al. |
| 5,632,893 A | 5/1997 | Brown et al. |
| 5,868,696 A | 2/1999 | Giesler et al. |
| 5,980,757 A | 11/1999 | Brown et al. |
| 5,980,760 A | 11/1999 | Min et al. |
| 6,304,767 B1 | 10/2001 | Soller et al. |
| 6,312,607 B1 | 11/2001 | Brown et al. |
| 6,471,855 B1 | 10/2002 | Odak et al. |
| 6,579,219 B2 | 6/2003 | Min et al. |
| 6,582,386 B2 | 6/2003 | Min et al. |
| 6,629,919 B2 | 10/2003 | Egozy et al. |
| 6,706,008 B2 | 3/2004 | Vishnoi et al. |
| 6,770,883 B2 | 8/2004 | McNeal et al. |
| 6,808,503 B2 | 10/2004 | Farrell et al. |
| 6,866,826 B2 | 3/2005 | Moore et al. |
| 6,884,228 B2 | 4/2005 | Brown et al. |
| 6,899,666 B2 | 5/2005 | Brown |
| 7,011,761 B2 | 3/2006 | Muller |
| 7,049,622 B1 | 5/2006 | Weiss |
| 7,081,082 B2 | 7/2006 | Scholz et al. |
| 7,150,834 B2 | 12/2006 | Mueth et al. |
| 7,186,230 B2 | 3/2007 | Briggs et al. |
| 7,186,231 B2 | 3/2007 | Takagi et al. |
| 7,211,037 B2 | 5/2007 | Briggs et al. |
| 7,294,513 B2 | 11/2007 | Wyatt |
| 7,297,272 B2 | 11/2007 | Min et al. |
| 7,347,948 B2 | 3/2008 | Dolecek et al. |
| 7,354,515 B2 | 4/2008 | Coull et al. |
| 7,381,291 B2 | 6/2008 | Tobe et al. |
| 7,422,693 B2 | 9/2008 | Carter et al. |
| 7,485,084 B2 | 2/2009 | Borgstrom et al. |
| 7,563,376 B2 | 7/2009 | Oishi |
| 7,648,639 B2 | 1/2010 | Holmes et al. |
| 7,806,845 B2 | 10/2010 | Arm et al. |
| 7,906,771 B2 | 3/2011 | Carter et al. |
| 7,951,059 B2 | 5/2011 | Sweat |
| 8,057,377 B2 | 11/2011 | Holmes et al. |
| 8,075,468 B2 | 12/2011 | Min et al. |
| 8,163,276 B2 | 4/2012 | Hedrick et al. |
| 8,287,742 B2 | 10/2012 | Holmes |
| 8,317,672 B2 | 11/2012 | Nash et al. |
| 8,337,379 B2 | 12/2012 | Fletcher et al. |
| 8,535,210 B2 | 9/2013 | Kolenbrander et al. |
| 8,758,211 B2 | 6/2014 | Nash et al. |
| 8,974,362 B2 | 3/2015 | Nash et al. |
| 9,011,687 B2 | 4/2015 | Swift et al. |
| 9,156,039 B2 | 10/2015 | Holmes et al. |
| 9,164,078 B2 | 10/2015 | Min et al. |
| 9,302,042 B2 | 4/2016 | Pages |
| 9,302,276 B2 | 4/2016 | Pesetsky et al. |
| 9,370,615 B2 | 6/2016 | Ragusa et al. |
| 9,399,182 B2 | 7/2016 | Pesetsky et al. |
| 9,550,016 B2 | 1/2017 | Gifford |
| 9,610,590 B2 | 4/2017 | Hamandi |
| 9,789,235 B2 | 10/2017 | Gifford et al. |
| 9,833,557 B2 | 12/2017 | Thill et al. |
| 9,895,482 B2 | 1/2018 | Kusters et al. |
| 10,086,128 B2 | 10/2018 | Kyle et al. |
| 10,166,322 B2 | 1/2019 | Sweat et al. |
| 10,238,787 B2 | 3/2019 | Takuwa |
| 10,293,097 B2 | 5/2019 | Murphy et al. |
| 10,399,881 B2 | 9/2019 | Donais et al. |
| 10,493,467 B2 | 12/2019 | Lundquist et al. |
| 10,518,007 B2 | 12/2019 | Kimura |
| 10,561,783 B2 | 2/2020 | Hamandi et al. |
| 2003/0070969 A1 | 4/2003 | Muller et al. |
| 2011/0003675 A1 | 1/2011 | Dolecek |
| 2011/0294641 A1 | 12/2011 | Dolecek et al. |
| 2013/0324815 A1 | 12/2013 | Jian et al. |
| 2014/0057771 A1 | 2/2014 | Case et al. |
| 2014/0378292 A1 | 12/2014 | Igarashi |
| 2015/0025341 A1 | 1/2015 | Sakota et al. |
| 2015/0068959 A1 | 3/2015 | Zheng |
| 2015/0104824 A1 | 4/2015 | Walker et al. |
| 2015/0219558 A1 | 8/2015 | Koudelka et al. |
| 2015/0367063 A1 | 12/2015 | Kimura |
| 2017/0153431 A1 | 6/2017 | Nguyen et al. |
| 2018/0043374 A1 | 2/2018 | Meinig et al. |
| 2018/0164141 A1 | 6/2018 | Bordignon et al. |
| 2018/0185772 A1 | 7/2018 | Karhiniemi et al. |
| 2019/0003873 A1 | 1/2019 | Araujo et al. |
| 2019/0030545 A1 | 1/2019 | Hamada et al. |
| 2019/0083696 A1 | 3/2019 | Igarashi |
| 2019/0313953 A1 | 10/2019 | Kusters et al. |
| 2019/0369008 A1 | 12/2019 | Kusters |

FOREIGN PATENT DOCUMENTS

| | | |
|---|---|---|
| WO | WO2012/091720 A1 | 7/2012 |
| WO | WO2017/048673 A1 | 3/2017 |
| WO | WO2018/053217 A1 | 3/2018 |
| WO | WO2018/154115 A2 | 8/2018 |
| WO | WO2019/047498 A1 | 3/2019 |
| WO | WO2019/165478 A1 | 8/2019 |
| WO | WO2020/002059 A1 | 1/2020 |
| WO | WO2020/055958 A1 | 3/2020 |

OTHER PUBLICATIONS

Extended European Search Report dated Oct. 12, 2020 (dated Oct. 12, 2020) for EP 20175601.

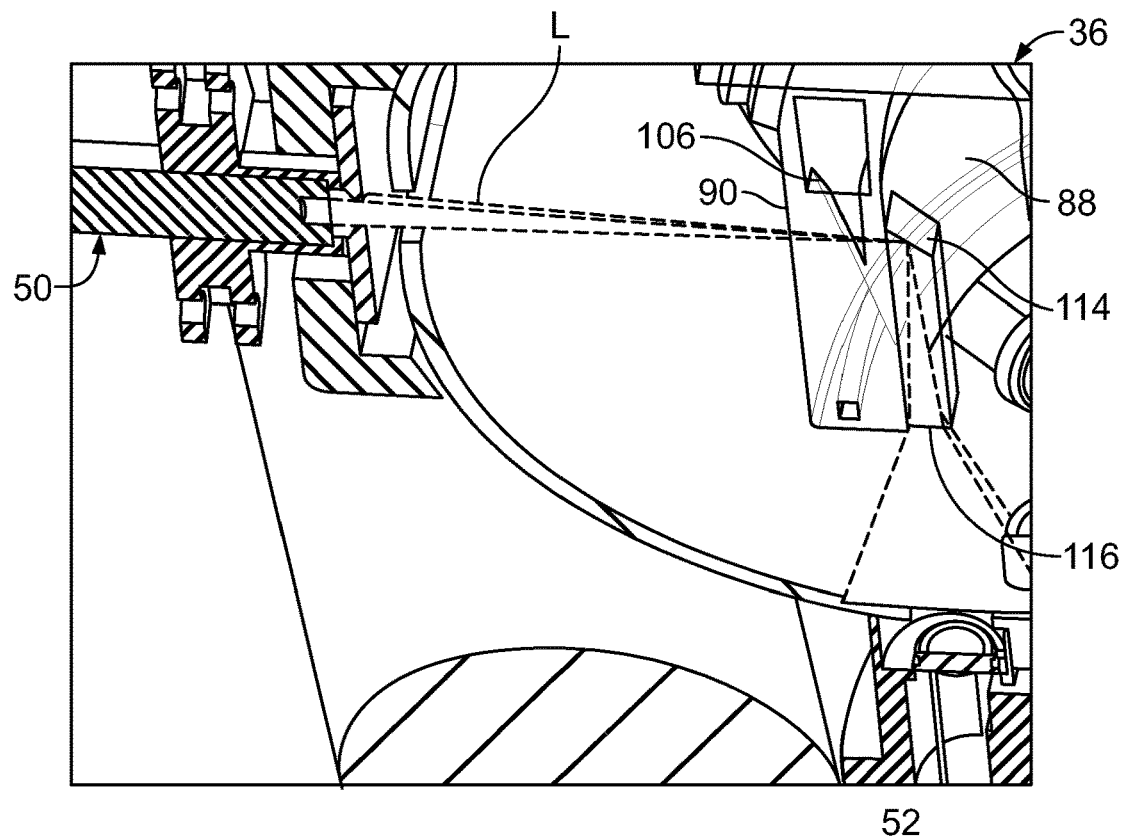
FIG. 7
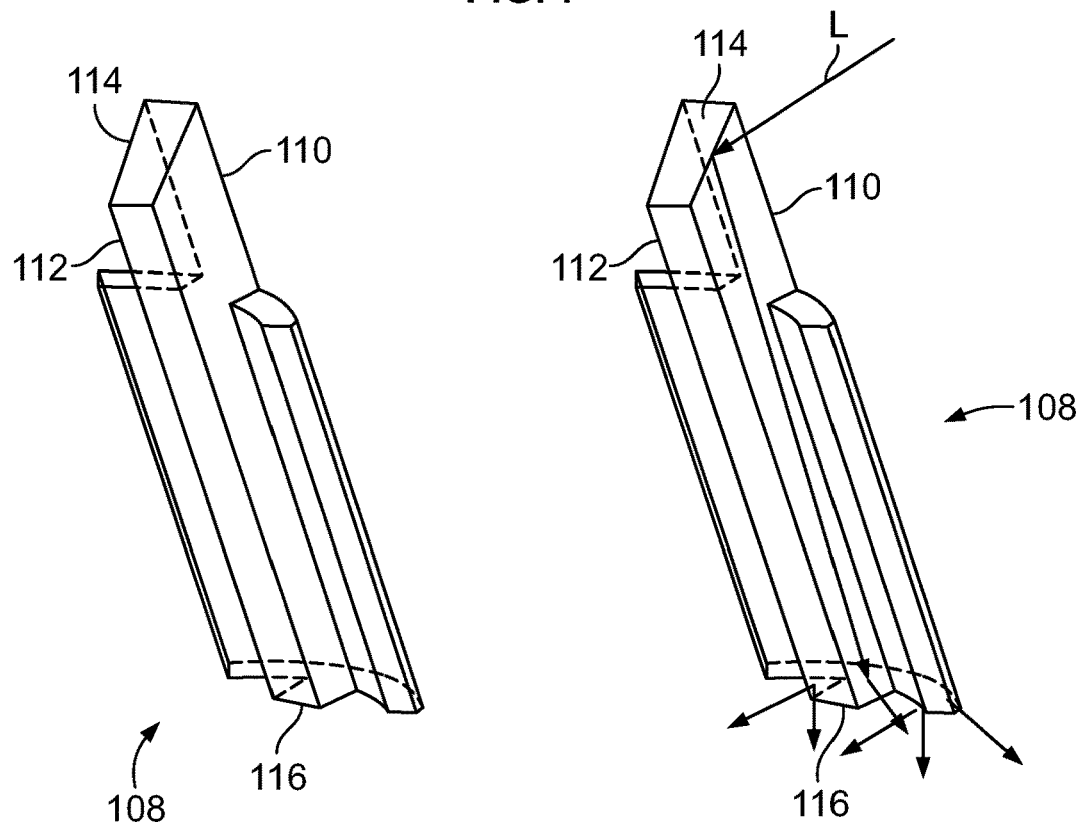
FIG. 19  FIG. 20

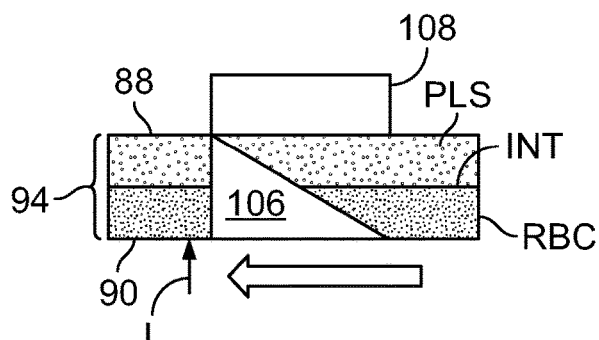 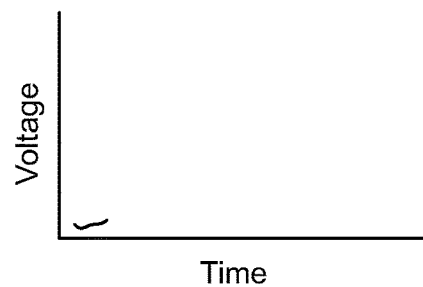
FIG. 29  FIG. 33
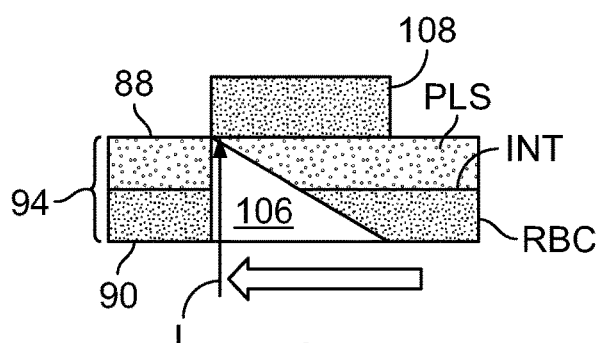 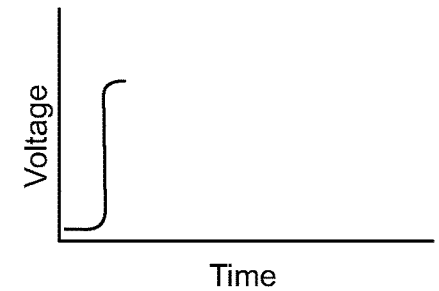
FIG. 30  FIG. 34
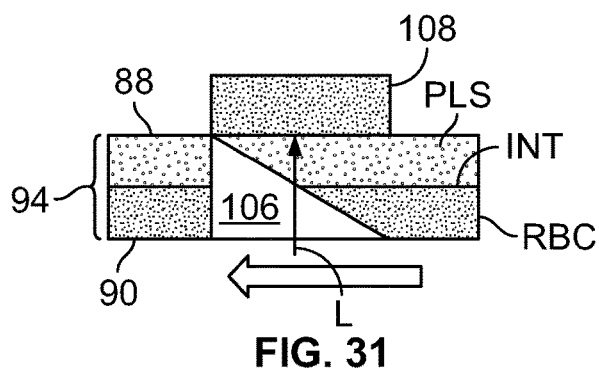 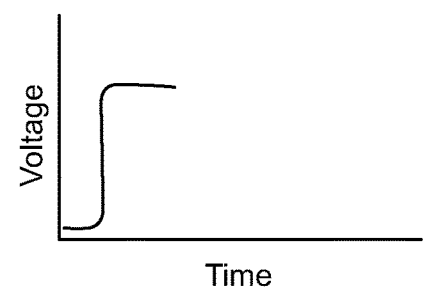
FIG. 31  FIG. 35
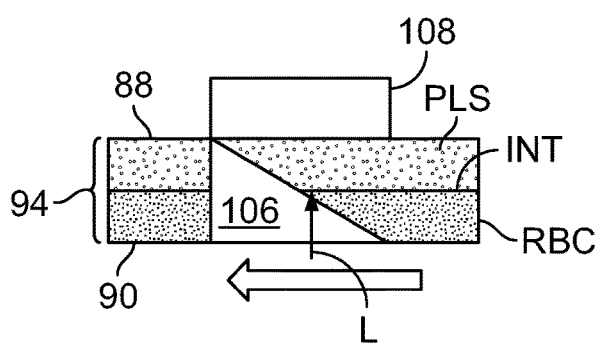 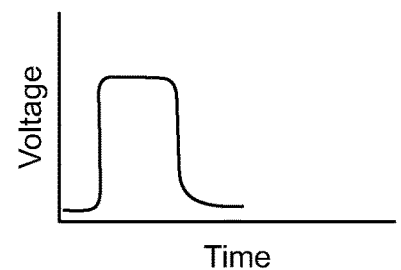
FIG. 32  FIG. 36

ADJUSTMENT OF TARGET INTERFACE LOCATION BETWEEN SEPARATED FLUID COMPONENTS IN A CENTRIFUGE

CROSS-REFERENCE TO RELATED APPLICATIONS

This application claims the benefit of and priority of U.S. Provisional Patent Application Ser. No. 62/851,712, filed May 23, 2019, the contents of which are incorporated by reference herein.

BACKGROUND

Field of the Disclosure

The present disclosure relates to centrifugal separation of a biological fluid. More particularly, the present disclosure relates to mid-processing adjustment of a target location for an interface between separated fluid components in a centrifuge.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

It is known to employ an optical sensor system to monitor the flow of blood and/or blood components through the flow circuit in the centrifuge and determine various characteristics of the flow. For example, U.S. Pat. No. 6,899,666 (which is hereby incorporated herein by reference) relates to an optical sensor system for viewing into the centrifuge chamber for detecting and controlling the location of an interface between separated blood components in a centrifuge. While this system functions satisfactorily, there remains an opportunity to provide optical monitoring systems which allow for a target interface location to be changed during a fluid separation procedure.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for adjusting a target location of an interface between separated fluid components continuously flowing through a centrifuge. The method includes separating fluid in a centrifuge into separated fluid components with an interface between the separated fluid components and with an initial target location of the interface as a current target location of the interface. One of the separated fluid components is removed from the centrifuge, with at least a portion of the separated fluid component flowing through a vessel and being exposed to light so as to cause an amount of light to be reflected by the separated fluid component in the vessel and received as a reflected light. A main wavelength of the reflected light is determined and compared to a maximum wavelength value. If the main wavelength of the reflected light is greater than the maximum wavelength value, the current target location of the interface is changed to a main wavelength-adjusted target location that becomes the current target location of the interface. If the main wavelength of the reflected light is not greater than the maximum wavelength value, the current target location of the interface is not changed based on the main wavelength of the reflected light.

In another aspect, a fluid separation device includes a centrifugal separator configured to receive a centrifugal separation chamber that is in fluid communication with a vessel. The device further includes a pump system configured to convey a fluid into the centrifugal separation chamber, remove a separated fluid component from the centrifugal separation chamber, and flow at least a portion of the separated fluid component through the vessel. An interface monitoring system of the device is configured to determine the position of an interface between separated fluid components continuously flowing through the centrifugal separation chamber, while a centrifuge outlet sensor of the device is configured to monitor the separated fluid component in the vessel. The device also includes a controller configured to control the pump system to convey a fluid into the centrifugal separation chamber and control the centrifugal separator to separate the fluid in the centrifugal separation chamber into separated fluid components, with an interface between the separated fluid components and with an initial target location of the interface as a current target location of the interface. The controller controls the pump system to remove one of the separated fluid components from the centrifugal separation chamber and flow at least a portion of said one of the separated fluid components through the vessel and controls the centrifuge outlet sensor to expose the vessel to light so as to cause an amount of light to be reflected by the separated fluid component in the vessel and received as a reflected light. The controller determines a main wavelength of the reflected light and compares the main wavelength of the reflected light to a maximum wavelength value. If the main wavelength of the reflected light is greater than the maximum wavelength value, the controller changes the current target location of the interface to a main wavelength-adjusted target location that becomes the current target location of the interface. If the main wavelength of the reflected light is not greater than the maximum wavelength value, the controller does not change the current target location of the interface based on the main wavelength of the reflected light.

In yet another aspect, a method is provided for adjusting a target location of an interface between separated fluid components continuously flowing through a centrifuge. The method includes separating fluid in a centrifuge into separated fluid components with an interface between the separated fluid components and with an initial target location of the interface as a current target location of the interface. One of the separated fluid components is removed from the centrifuge, with at least a portion of it flowing through a vessel, and with the vessel being exposed to light so as to cause an amount of light to be transmitted through the separated fluid component in the vessel and received as a transmitted light. An optical density of the separated fluid component in the vessel is determined based at least in part on the transmitted light and compared to a maximum optical density value. If the optical density of the separated fluid component in the vessel is greater than the maximum optical density value, the current target location of the interface is changed to an upper limit-adjusted target location that becomes the current target location of the interface. If the optical density of the separated fluid component in the vessel is not greater than said maximum optical density value, the current target location of the interface is not changed to the upper limit-adjusted target location.

In a further aspect, a fluid separation device includes a centrifugal separator configured to receive a centrifugal separation chamber in fluid communication with a vessel. The device also includes a pump system configured to convey a fluid into the centrifugal separation chamber, remove a separated fluid component from the centrifugal separation chamber, and flow at least a portion of the separated fluid component through the vessel. An interface monitoring system of the device is configured to determine the position of an interface between separated fluid components continuously flowing through the centrifugal separation chamber, while a centrifuge outlet sensor of the device is configured to monitor a separated fluid component in the vessel. The device further includes a controller configured to control the pump system to convey a fluid into the centrifugal separation chamber, control the centrifugal separator to separate the fluid in the centrifugal separation chamber into separated fluid components with an interface between the separated fluid components and with an initial target location of the interface as a current target location of the interface. The controller controls the pump system to remove one of the separated fluid components from the centrifugal separation chamber and flow at least a portion of said one of the separated fluid components through the vessel, and controls the centrifuge outlet sensor to expose the vessel to light so as to cause an amount of light to be transmitted through the separated fluid component in the vessel and received as a transmitted light. The controller determines an optical density of the separated fluid component in the vessel and compares the optical density of the separated fluid component in the vessel to a maximum optical density value. If the optical density of the separated fluid component in the vessel is greater than the maximum optical density value, the controller changes the current target location of the interface to an upper limit-adjusted target location that becomes the current target location of the interface. If the optical density of the separated fluid component in the vessel is not greater than the maximum optical density value, the controller does not change the current target location of the interface to the upper limit-adjusted target location.

BRIEF DESCRIPTION OF THE DRAWINGS

FIG. 7 is a perspective view of the centrifugal separator of FIG. 3, with selected portions thereof broken away to show the light source and light detector of the interface monitoring system;

FIG. 19 is a perspective view of a prismatic reflector used in combination with any of the centrifugal separation chambers of FIGS. 8-15;

FIG. 20 is a perspective view of the prismatic reflector of FIG. 19, showing light being transmitted therethrough;

FIGS. 29-32 are diagrammatic views of the ramp and prismatic reflector passing through the path of light from the light source during a separation procedure;

FIGS. 33-36 are diagrammatic views of the voltage output or signal transmitted by the light detector during the conditions shown in FIGS. 29-32, respectively;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-46 show components of a blood or fluid separation system that embodies various aspects of the present subject matter. While the system may be described herein in terms of its use in separating blood into two or more components, it should be understood that systems according to the present disclosure can be used for processing a variety of biological or bodily fluids, including fluids containing both bodily and non-bodily fluids (e.g., anticoagulated blood).

Figure 1:
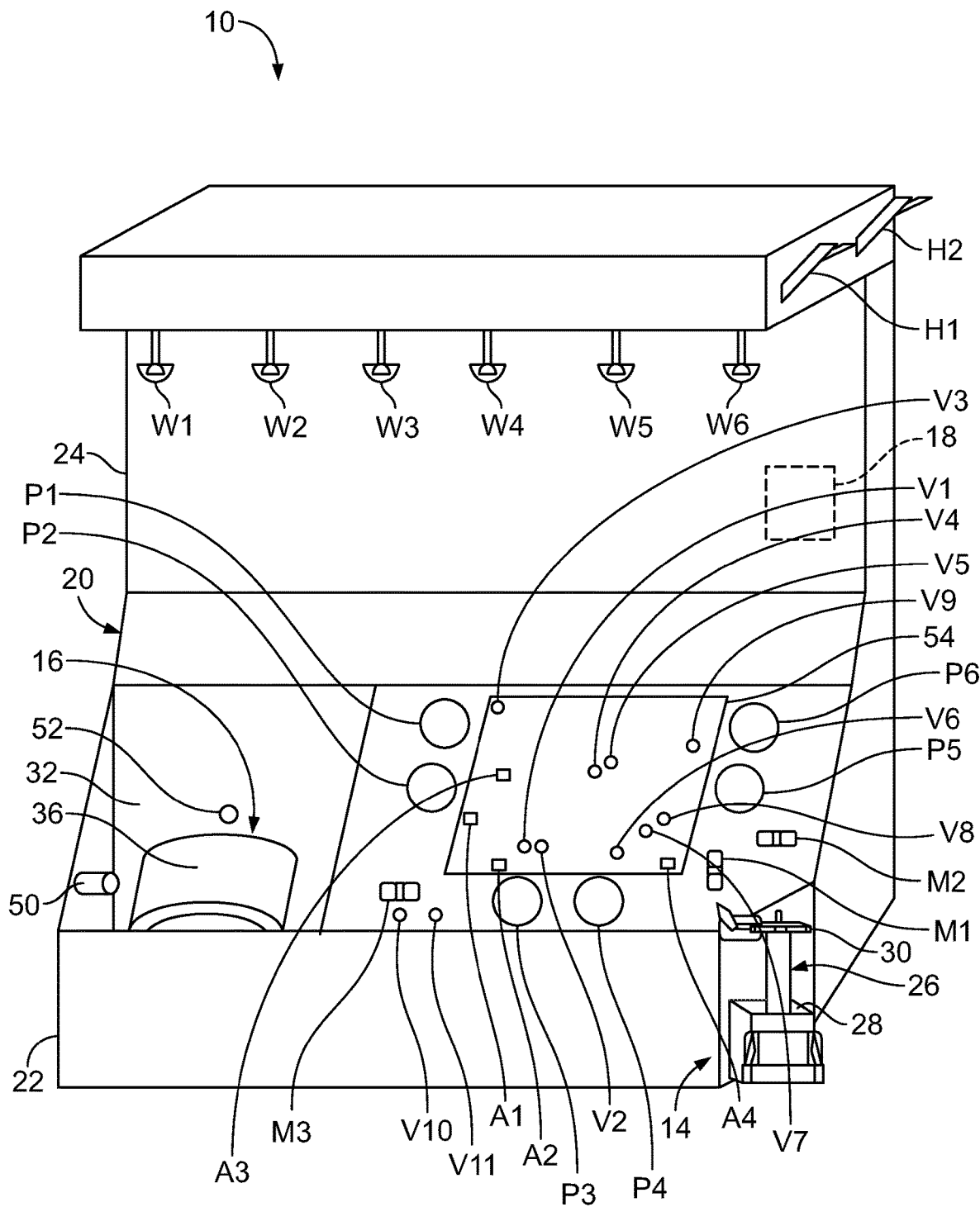
FIG. 1 is a perspective view of an exemplary fluid separation device that comprises a component of a fluid separation system according to an aspect of the present disclosure.
Figure 2:
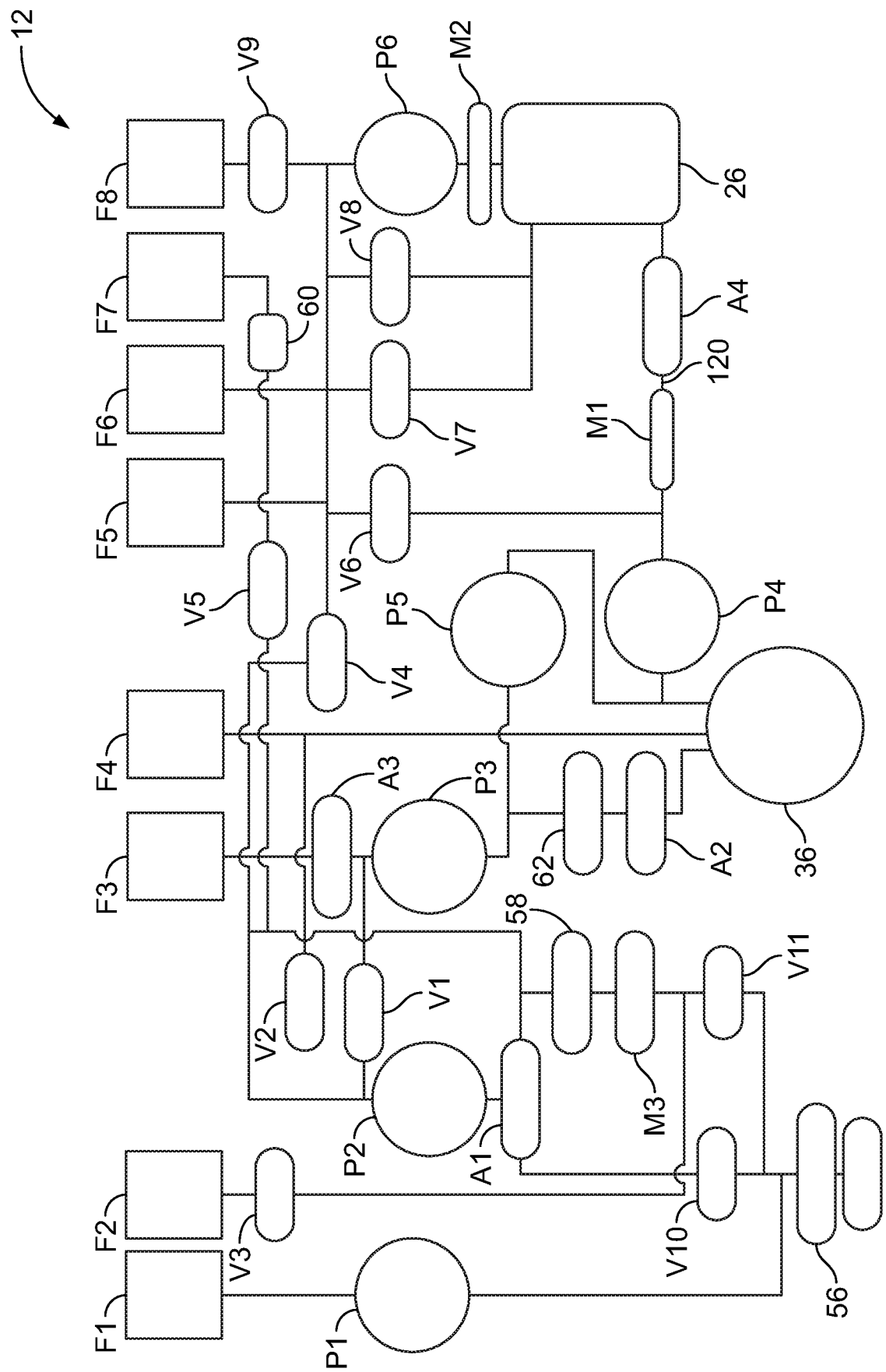
FIG. 2 is a schematic view of an exemplary disposable fluid flow circuit that may be mounted to the fluid separation device of FIG. 1 to complete a fluid separation system according to an aspect of the present disclosure.

Generally speaking, the system includes two principal components, a durable and reusable fluid separation device 10 (FIG. 1) and a disposable fluid flow circuit 12 (FIG. 2). The fluid separation device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid separation device 10 to perform a fluid processing and collection procedure selected by the operator. The interface adjustment principles described herein are not limited to any particular fluid separation procedures, so no complete fluid separation procedure will be described in detail herein. However, reference may be made to PCT Patent Application Publication No. WO 2018/053217 A1 (which is hereby incorporated herein by reference) for descriptions of various exemplary fluid separation procedures that may be carried out using the system described herein and which may be practiced in combination with the interface adjustment principles described herein.

I. The Durable Fluid Separation Device

The fluid separation device 10 (FIG. 1) is configured as a durable item that is capable of long-term use. It should be understood that the fluid separation device 10 of FIG. 1 is merely exemplary of one possible configuration and that fluid separation devices according to the present disclosure may be differently configured. For example, it is within the scope of the present disclosure for the fluid separation device to omit a spinning membrane separator drive unit 14 and to include only a centrifugal separator 16.

In the illustrated embodiment, the fluid separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the centrifugal separator 16, the controller 18, and selected other components of the fluid separation device 10 will be described in greater detail.

In the illustrated embodiment, the generally horizontal portion 22 is intended to rest on an elevated, generally horizontal support surface (e.g., a countertop or a tabletop), but it is also within the scope of the present disclosure for the case 20 to include a support base to allow the case 20 to be appropriately positioned and oriented when placed onto a floor or ground surface. It is also within the scope of the present disclosure for the case 20 to be mounted to a generally vertical surface (e.g., a wall), by either fixedly or removably securing the generally vertical portion 24 of the case 20 to the surface.

The case 20 may be configured to assume only the position or configuration of FIG. 1 or may be configured to move between two or more positions or configurations. For example, in one embodiment, the generally horizontal and vertical portions 22 and 24 are joined by a hinge or pivot, which allows the case 20 to be moved between a functional or open configuration (FIG. 1) in which the generally vertical portion 24 is oriented at approximately 90 degrees to the generally horizontal portion 22 and a transport or closed configuration in which the generally vertical portion 24 is rotated about the hinge to approach the generally horizontal portion 22. In such a reconfigurable embodiment, the generally vertical portion 24 may be considered to be the lid of the case 20, while the generally horizontal portion 22 may be considered to be the base. If the case 20 is so reconfigurable, then it may include a latch for releasably locking the case 20 in its closed configuration and/or a handle, which the operator can grasp for transporting the case 20 in its closed configuration.

While it may be advantageous for the fluid separation device 10 to be embodied in a compact, portable case 20, it is also within the scope of the present disclosure for the fluid separation device to be embodied in a larger case or fixture that is intended to be installed in a single location and remain in that location for an extended period of time. If the fluid separation device is provided as a fixture, it may be provided with more components and functionality than a more portable version.

A. Spinning Membrane Separator Drive Unit

The illustrated fluid separation device 10 includes a spinner support or spinning membrane separator drive unit 14 (FIG. 1) for accommodating a generally cylindrical spinning membrane separator 26 of a fluid flow circuit 12 (FIG. 2). U.S. Pat. No. 5,194,145 (which is hereby incorporated herein by reference) describes an exemplary spinning membrane separator drive unit that would be suitable for incorporation into the fluid separation device 10, but it should be understood that the spinning membrane separator drive unit 14 may be differently configured without departing from the scope of the present disclosure. The interface determination principles described herein may be practiced in the absence of a spinning membrane separator, so the spinning membrane separator drive unit 14 is not described in detail herein.

B. Centrifugal Separator

Figure 3:
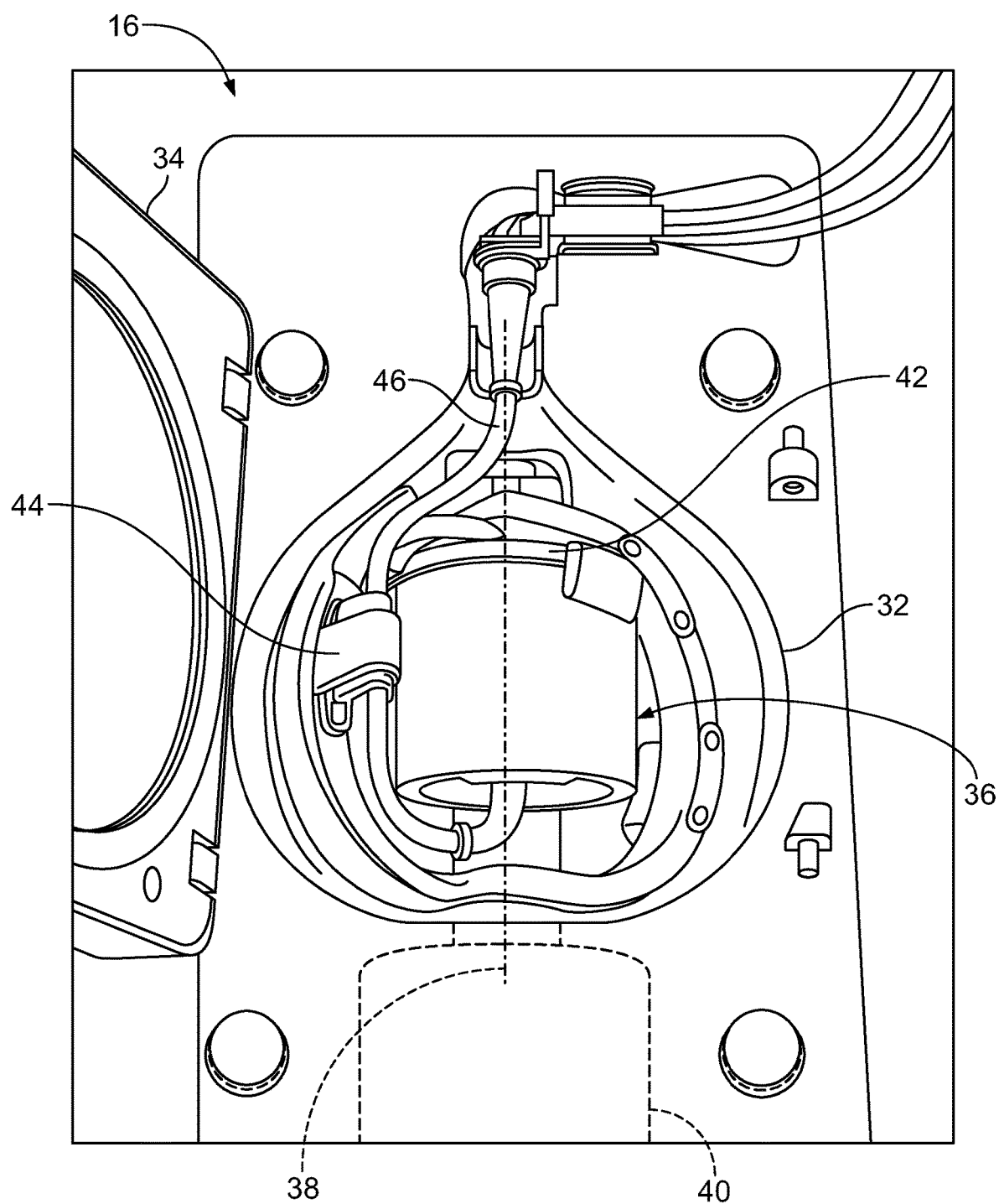
FIG. 3 is a perspective view of an exemplary centrifugal separator of the fluid separation device of FIG. 1, with the centrifugal separation chamber of a fluid flow circuit mounted therein.

As for the centrifugal separator 16, it includes a centrifuge compartment 32 that may receive the other components of the centrifugal separator 16 (FIG. 3). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

Figure 4:
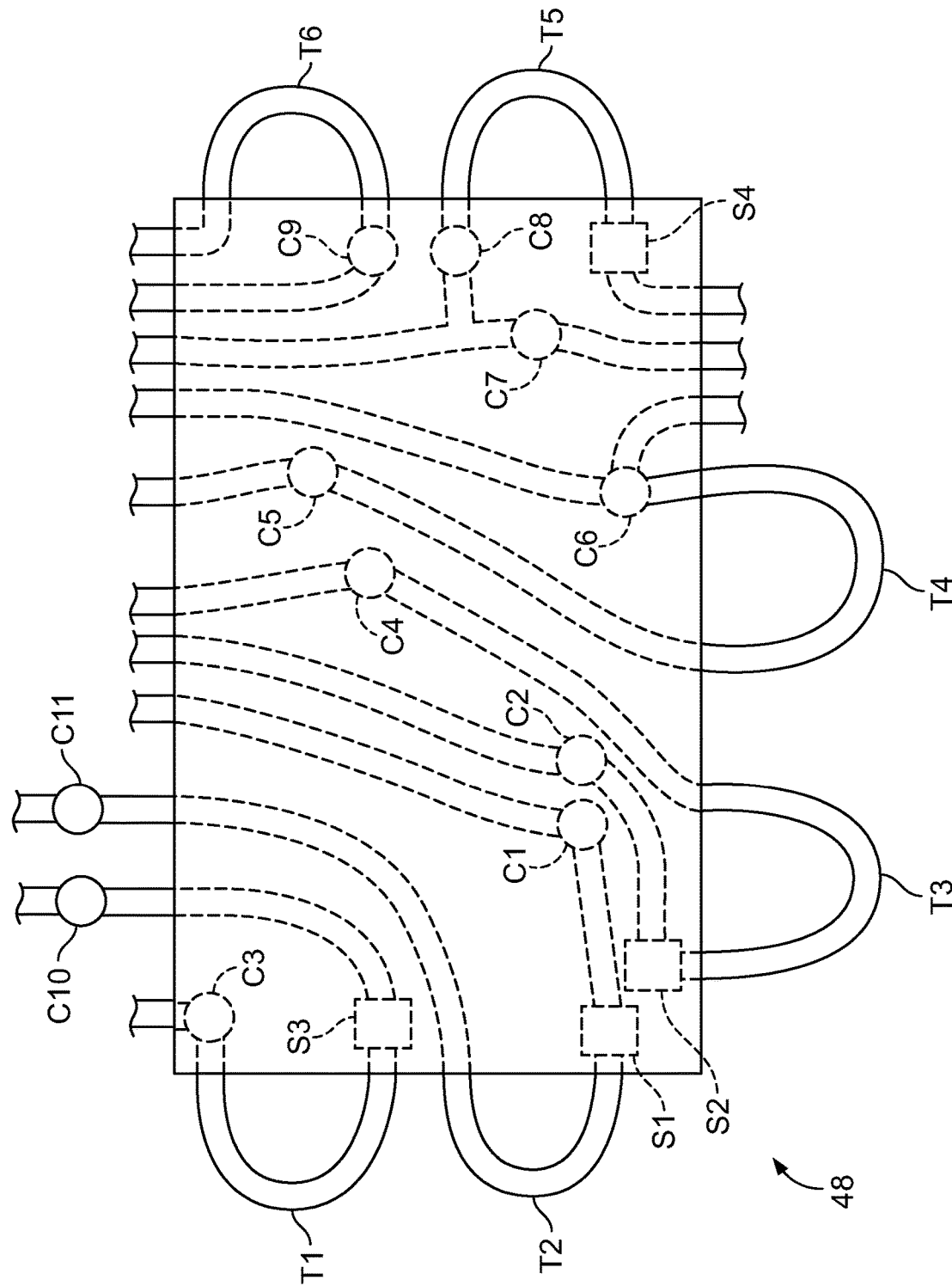
FIG. 4 is a top plan view of an exemplary cassette of a fluid flow circuit, which can be actuated to perform a variety of different fluid processing procedures in association with the fluid separation device shown in FIG. 1.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX system manufactured by Fenwal, Inc. of Lake Zurich, Ill., which is an affiliate of Fresenius Kabi AG of Bad Homburg, Germany, as described in greater detail in U.S. Pat. No. 8,075,468, which is hereby incorporated herein by reference. More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 4). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

Figure 6:
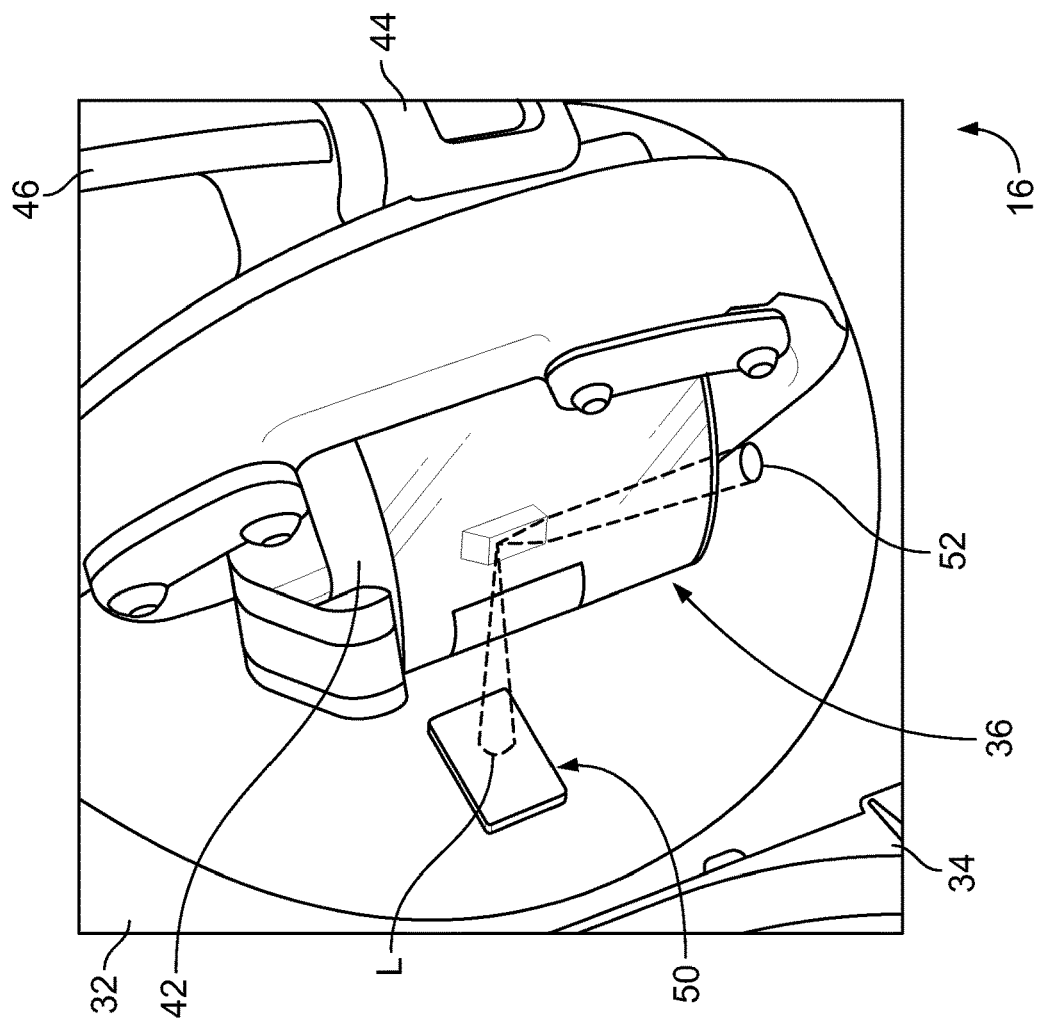
FIG. 6 is a perspective view of the centrifugal separator of FIG. 3, with the light source operating to transmit a light beam to a light detector of the interface monitoring system.
Figure 5:
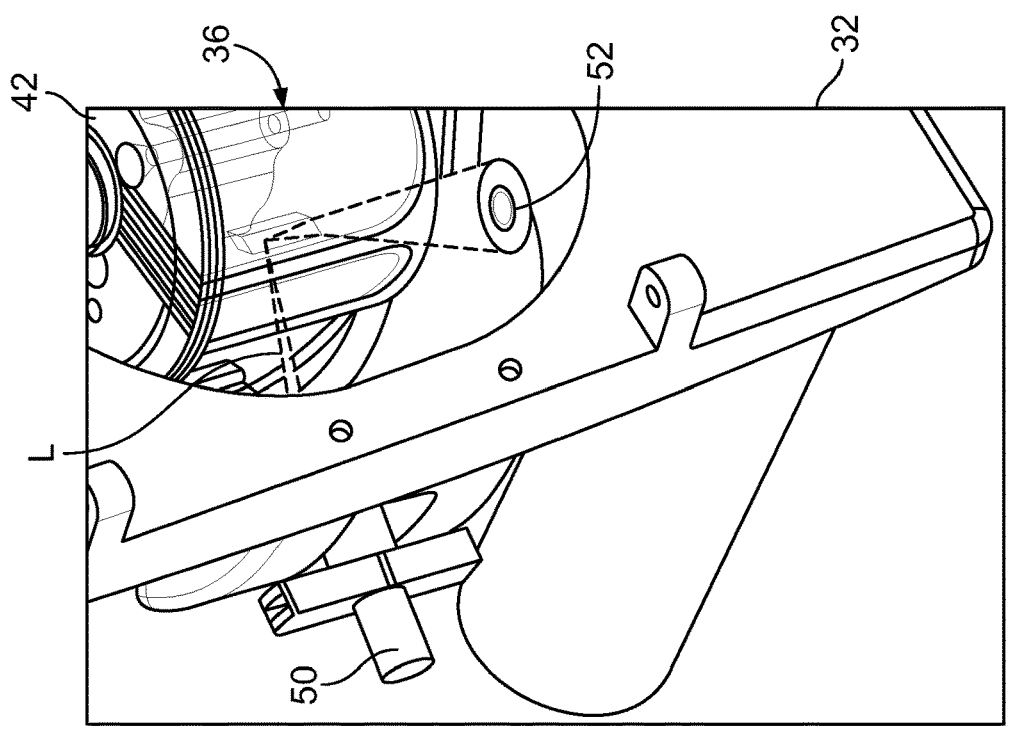
FIG. 5 is a perspective view of the centrifugal separator of FIG. 3, with selected portions thereof broken away to show a light source of an interface monitoring system.

A fluid is introduced into the centrifugal separation chamber 36 by the umbilicus 46, with the fluid being separated (e.g., into a layer of less dense components, such as platelet-rich plasma, if the fluid is blood, and a layer of more dense components, such as packed red blood cells, if the fluid is blood) within the centrifugal separation chamber 36 as a result of centrifugal forces as it rotates. Components of an interface monitoring system may be positioned within the centrifuge compartment 32 to oversee separation of blood within the centrifugal separation chamber 36. As shown in FIGS. 5-7, the interface monitoring system may include a light source 50 and a light detector 52, which is positioned and oriented to receive at least a portion of the light emitted by the light source 50. Preferably, the light source 50 and the light detector 52 are positioned on stationary surfaces of the centrifuge compartment 32, but it is also within the scope of the present disclosure for one or both to be mounted to a movable component of the centrifugal separator 16 (e.g., to the yoke member 44, which rotates at a one omega speed).

The orientation of the various components of the interface monitoring system depends at least in part on the particular configuration of the centrifugal separation chamber 36, which will be described in greater detail herein. In general, though, the light source 50 emits a light beam (e.g., a laser light beam) through the separated fluid components within the centrifugal separation chamber 36 (which may be formed of a material that substantially transmits the light or at least a particular wavelength of the light without absorbing it). A portion of the light reaches the light detector 52, which transmits a signal to the controller 18 that is indicative of the location of an interface between the separated fluid components. If the controller 18 determines that the interface is in the wrong location (which can affect the separation efficiency of the centrifugal separator 16 and/or the quality of the separated blood components), then it can issue commands to the appropriate components of the fluid separation device 10 to modify their operation so as to move the interface to the proper location. The interface monitoring system works in combination with a centrifuge outlet sensor M1 that allows for adjustment of the target interface location, as will be described in greater detail herein.

C. Other Components of The Fluid Separation Device

In addition to the spinning membrane separator drive unit 14 and the centrifugal separator 16, the fluid separation device 10 may include other components compactly arranged to aid fluid processing.

The generally horizontal portion 22 of the case 20 of the illustrated fluid separation device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is hereby incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 52 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the fluid source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The fluid separation device 10 may also include a plurality of pumps P1-P6 to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12. In one embodiment, all or a portion of the cassette station 54 may be capable of translational motion in and out of the case 20 to allow for automatic loading of the tubing loops T1-T6 into the associated pump P1-P6.

The illustrated fluid separation device 10 also includes a centrifuge outlet sensor M1 for determining one or more properties of fluids flowing out of the centrifugal separator 16. If the fluid flowing out of the centrifugal separator 16 includes red blood cells, the centrifuge outlet sensor M1 may be configured to determine the hematocrit of the fluid. If the fluid flowing out of the centrifugal separator 16 is platelet-rich plasma, the centrifuge outlet sensor M1 may be configured to determine the platelet concentration of the platelet-rich plasma. The centrifuge outlet sensor M1 may detect the one or more properties of a fluid by optically monitoring the fluid as it flows through tubing of the fluid flow circuit 12 or by any other suitable approach. The controller 18 may receive signals from the centrifuge outlet sensor M1 that are indicative of the one or more properties of fluid flowing out of the centrifugal separator 16 and use the signals to optimize the separation procedure based upon that property or properties, as will be described in greater detail herein.

The illustrated fluid separation device 10 further includes a spinner outlet sensor M2, which accommodates tubing of a fluid flow circuit 12 that flows a separated fluid component out of a spinning membrane separator 26 of the fluid flow circuit 12.

The illustrated fluid separation device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F8 of the fluid flow circuit 12 (FIG. 2). The containers F1-F8 receive a fluid to be separated, fluid components separated during processing, or intravenous fluids or additive fluids. Each weight scale W1-W6 transmits to the controller 18 a signal that is indicative of the weight of the fluid within the associated container F1-F8 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

D. Controller

The fluid separation device 10 includes a controller 18, which is suitably configured and/or programmed to control operation of the fluid separation device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid separation device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid separation device 10, conveying fluid through the fluid flow circuit 12 to a location for separation (i.e., into the spinning membrane separator 26 or the centrifugal separation chamber 36 of the fluid flow circuit 12), separating the fluid into two or more components as desired, and conveying the separated components into storage containers, to a second location for further separation (e.g., into whichever of the spinning membrane separator 26 and centrifugal separation chamber 36 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump P1-P6 to convey fluid through a portion of the fluid flow circuit 12 at a particular flow rate. Hence, while it may be described herein that a particular component of the fluid separation device 10 (e.g., the spinning membrane separator drive unit 14 or the centrifugal separator 16) performs a particular function, it should be understood that that component is being controlled by the controller 18 to perform that function.

For procedures that call for the use of both the centrifugal separator 16 and the spinning membrane separator drive unit 14, a properly programmed controller 18 is especially important to coordinate the operation of these two components, along with the other components of the fluid separation device 10 to ensure that flow to and from the centrifugal separator 16 and spinning membrane separator drive unit 14 is at the proper level and that the components are functioning properly to process the fluid circulating through the fluid flow circuit 12.

Before, during, and after a procedure, the controller 18 may receive signals from various components of the fluid separation device 10 (e.g., the pressure sensors A1-A4) to monitor various aspects of the operation of the fluid separation device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring system and the centrifuge outlet sensor M1. The signals that the controller 18 receives from the light detector 52 are indicative of the location of an interface between the separated blood components within the centrifugal separation chamber 36, while the signals from the centrifuge outlet sensor M1 indicate whether the target interface location should be adjusted. If the controller 18 determines that the interface is in the wrong location, then it can issue commands to the appropriate components of the fluid separation device 10 to modify their operation so as to move the interface to the proper location. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 2), it is intended to be a sterile, single use, disposable item. Before beginning a given fluid separation procedure, the operator loads various components of the fluid flow circuit 12 in the case 20 in association with the fluid separation device 10. The controller 18 implements the procedure based upon preset protocols, taking into account other input from the operator. Upon completing the procedure, the operator removes the fluid flow circuit 12 from association with the fluid separation device 10. The portions of the fluid flow circuit 12 holding the collected fluid component or components (e.g., collection containers or bags) are removed from the case 20 and retained for storage, transfusion, or further processing. The remainder of the fluid flow circuit 12 is removed from the case 20 and discarded.

A variety of different disposable fluid flow circuits may be used in combination with the blood separation device 10, with the appropriate fluid flow circuit depending on the separation procedure to be carried out using the system. Generally speaking, though, the fluid flow circuit 12 includes a cassette 48 (FIG. 4), to which the other components of the fluid flow circuit 12 are connected by flexible tubing. The other components may include a plurality of fluid containers F1-F8 (for holding fluid to be processed, a separated fluid component, an intravenous fluid, or an additive solution, for example), one or more fluid source access devices (e.g., a connector for accessing blood within a fluid container), and a spinning membrane separator 26 and/or a centrifugal separation chamber 36 (FIGS. 8-15).

B. Cassette and Tubing

The cassette 48 (FIG. 4) provides a centralized, programmable, integrated platform for all the pumping and many of the valving functions required for a given fluid separation procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the fluid separation device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the fluid separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, but in one embodiment, a different one of the pumps P1-P6 may be configured to serve as an anticoagulant pump P1, a source pump P2, a saline pump P3, a spinner pump P4, a red blood cell pump P5, and an additive pump P6. Certain procedures may require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F8, the spinning membrane separator 26, and the centrifugal separation chamber 36. The number and content of the various fluid containers F1-F8 depends upon the procedure for which the fluid flow circuit 12 is used. The tubing connected to the centrifugal separation chamber 36 (which includes one inlet tube and two outlet tubes) may be aggregated into an umbilicus 46 (FIG. 3) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIG. 2, a manual clamp 56 may be associated with a line or lines leading to the blood source and/or fluid recipient, a return line filter 58 (e.g., a microaggregate filter) may be associated with a line leading to a fluid recipient, a filter 60 may be positioned upstream of one or more of the fluid containers to remove a substance (e.g., leukocytes) from a separated component (e.g., red blood cells or platelets) flowing into the fluid container, and/or an air trap 62 may be positioned on a line upstream of the centrifugal separation chamber 36.

C. Centrifugal Separation Chamber

Figure 8:
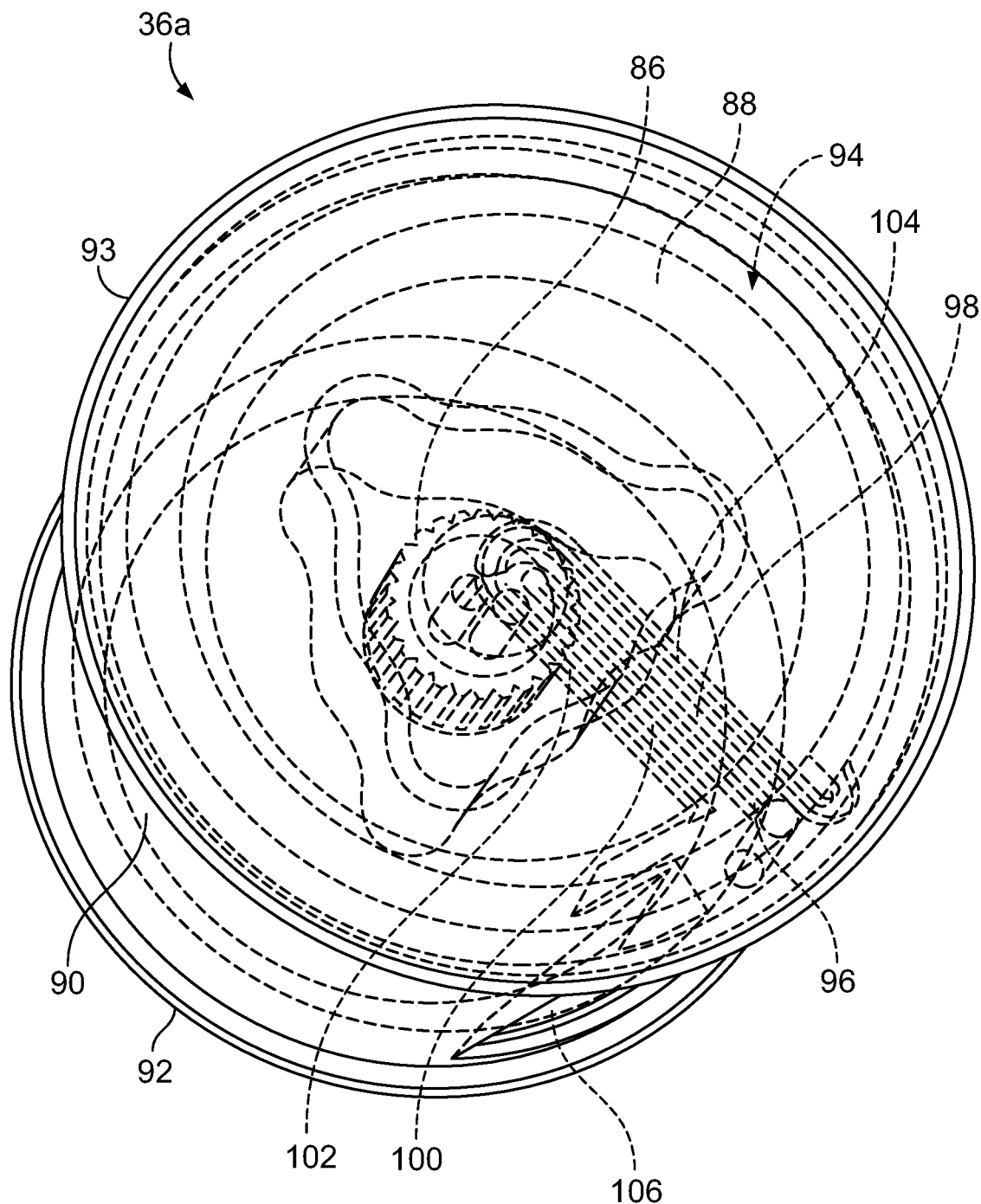
FIG. 8 is a perspective view of an exemplary centrifugal separation chamber of a fluid flow circuit.
Figure 9:
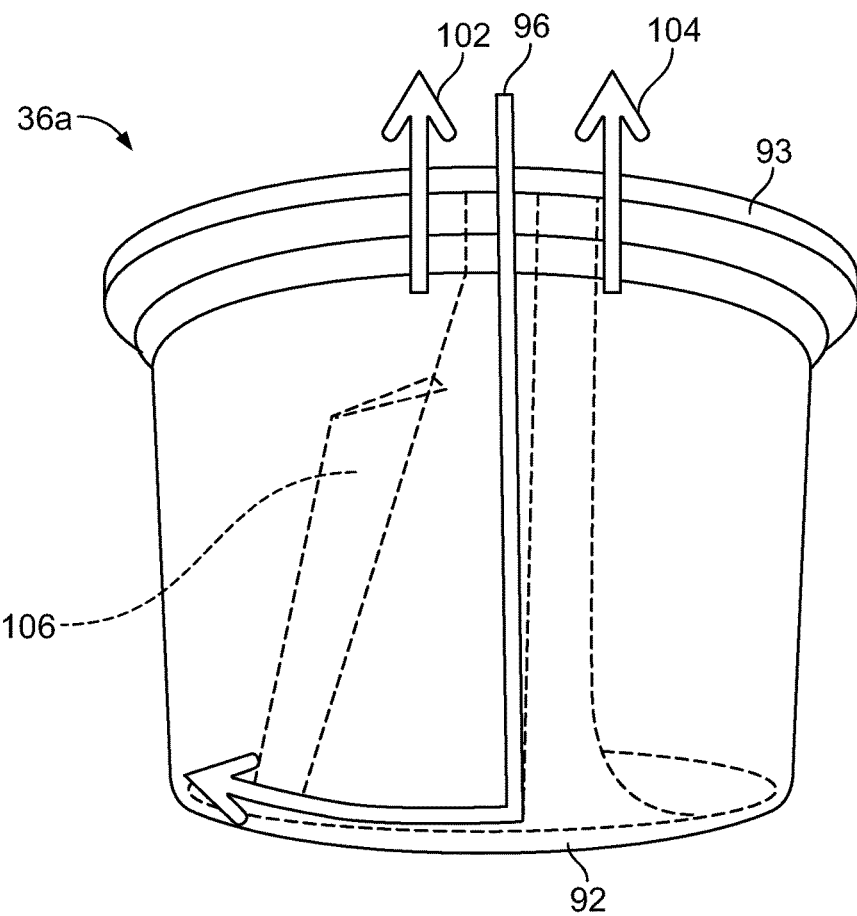
FIG. 9 is a front elevational view of the centrifugal separation chamber of FIG. 8.
Figure 10:
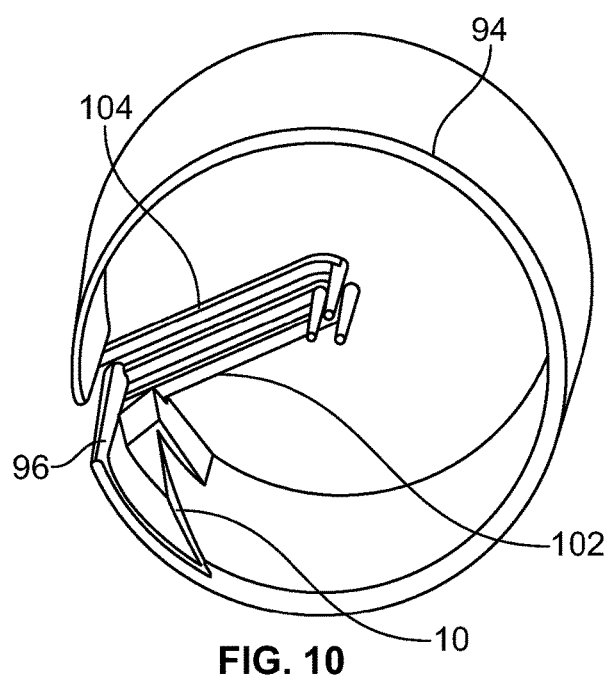
FIG. 10 is a bottom perspective view of the fluid flow path through the centrifugal separation chamber of FIG. 8.

An exemplary centrifugal separation chamber 36a is shown in FIGS. 8 and 9, while FIG. 10 illustrates the fluid flow path defined by the centrifugal separation chamber 36a. In the illustrated embodiment, the body of the centrifugal separation chamber 36a is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the fluid separation process are preformed in a single, injection molded operation. Alternatively, the centrifugal separation chamber 36a can be formed by separate molded parts, either by nesting cup-shaped subassemblies or two symmetric halves.

The underside of the centrifugal separation chamber 36a includes a shaped receptacle 86 that is suitable for receiving an end of the umbilicus 46 of the fluid flow circuit 12 (FIG. 3). A suitable receptacle 86 and the manner in which the umbilicus 46 may cooperate with the receptacle 86 to deliver fluid to and remove fluid from the centrifugal separation chamber 36a are described in greater detail in U.S. Pat. No. 8,075,468.

The illustrated centrifugal separation chamber 36a has radially spaced apart inner (low-g) and outer (high-g) side wall portions 88 and 90, a bottom or first end wall portion 92, and a cover or second end wall portion 93. The cover 93 comprises a simple flat part that can be easily welded or otherwise secured to the body of the centrifugal separation chamber 36a. Because all features that affect the separation process are incorporated into one injection molded component, any tolerance differences between the cover 93 and the body of the centrifugal separation chamber 36a will not affect the separation efficiencies of the centrifugal separation chamber 36a. The wall portions 88 and 90, the bottom 92, and the cover 93 together define an enclosed, generally annular channel 94 (FIG. 10).

An inlet 96 communicating with the channel 94 is defined between opposing interior radial walls 98 and 100. One of the interior walls 98 joins the outer (high-g) wall portion 90 and separates the upstream and downstream ends of the channel 94. The interior walls 98 and 100 define the inlet passageway 96 of the centrifugal separation chamber 36a which, in one flow configuration, allows fluid to flow from the umbilicus 46 to the upstream end of the channel 94.

The illustrated centrifugal separation chamber 36a further includes first and second outlets 102 and 104, respectively, which may be defined by opposing surfaces of interior radial walls. Both the first and second outlets 102 and 104 extend radially inward from the channel 94. The first outlet 102 extends radially inward from an opening which, in the illustrated embodiment, is located at the inner side wall portion 88, while the second outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

Figure 11:
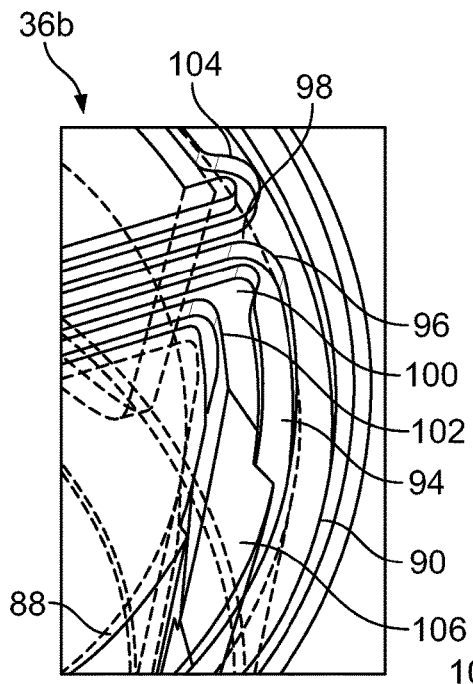
FIG. 11 is a perspective view of another embodiment of a centrifugal separation chamber of a fluid flow circuit.
Figure 12:
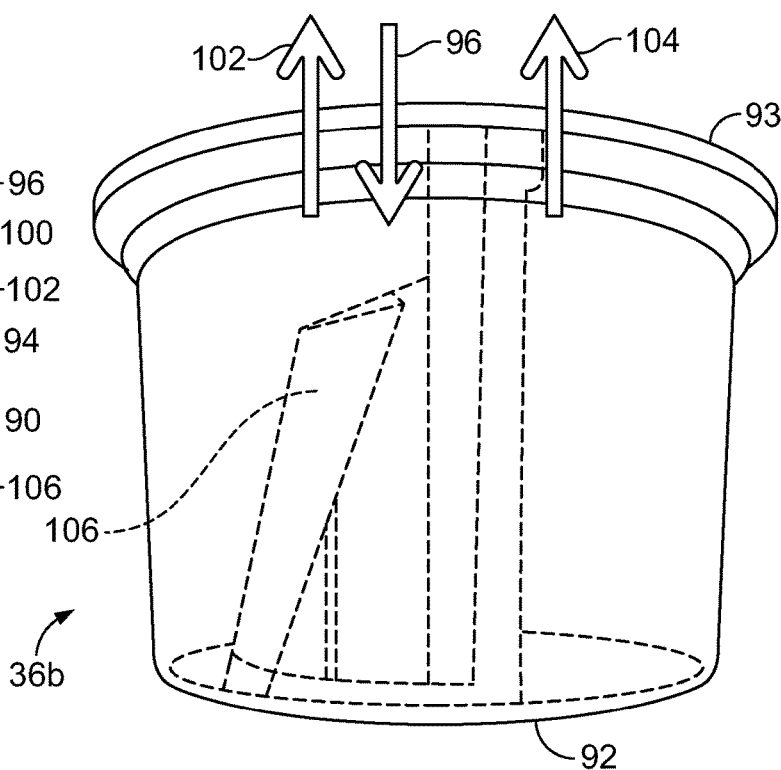
FIG. 12 is a front elevational view of the centrifugal separation chamber of FIG. 11.
Figure 13:
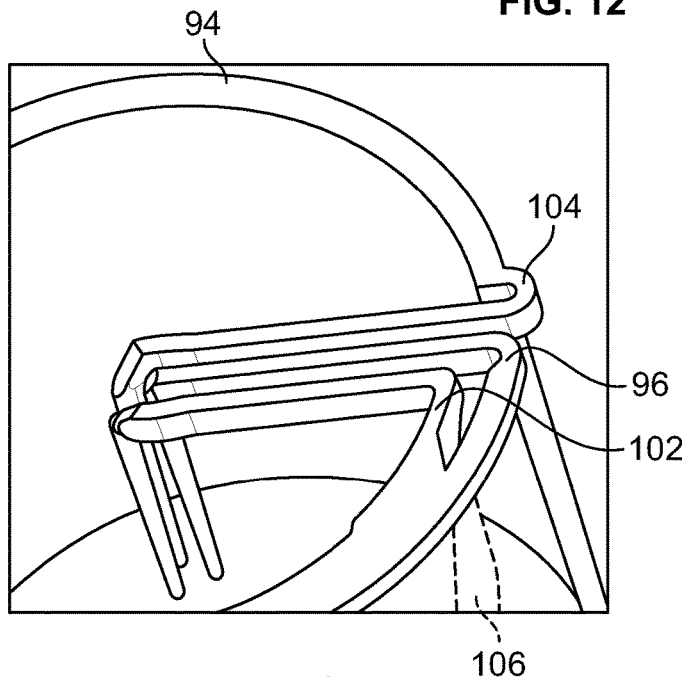
FIG. 13 is a top perspective view of the fluid flow path through the centrifugal separation chamber of FIG. 11.

It should be understood that the centrifugal separation chamber 36a illustrated in FIG. 8 is merely exemplary and that the centrifugal separation chamber 36 may be differently configured without departing from the scope of the present disclosure. For example, FIGS. 11 and 12 show an alternative embodiment of a centrifugal separation chamber 36b, while FIG. 13 illustrates the fluid flow path defined by the centrifugal separation chamber 36b. The centrifugal separation chamber 36b is similar to the centrifugal separation chamber 36a except for the location at which the inlet 96 opens into the channel 94. In the centrifugal separation chamber 36a of FIG. 8, the inlet 96 opens into the channel 94 adjacent to the first end wall portion 92 (while the outlets 102 and 104 open into the channel 94 adjacent to the second end wall portion 93), as best shown in FIGS. 9 and 10. In contrast, the inlet 96 of the centrifugal separation chamber 36b of FIG. 11 opens into the channel 94 adjacent to the second end wall portion 93 (along with the outlets 102 and 104), as best shown in FIGS. 12 and 13. The location at which the inlet 96 opens into the channel 94 may affect the separation of fluid within the channel 94, so the centrifugal separation chamber 36a of FIG. 8 may be preferable for certain procedures or for use in combination with certain fluid separation devices, while the centrifugal separation chamber 36b of FIG. 11 may be preferable for other procedures or for use in combination with other fluid separation devices.

Figure 14:
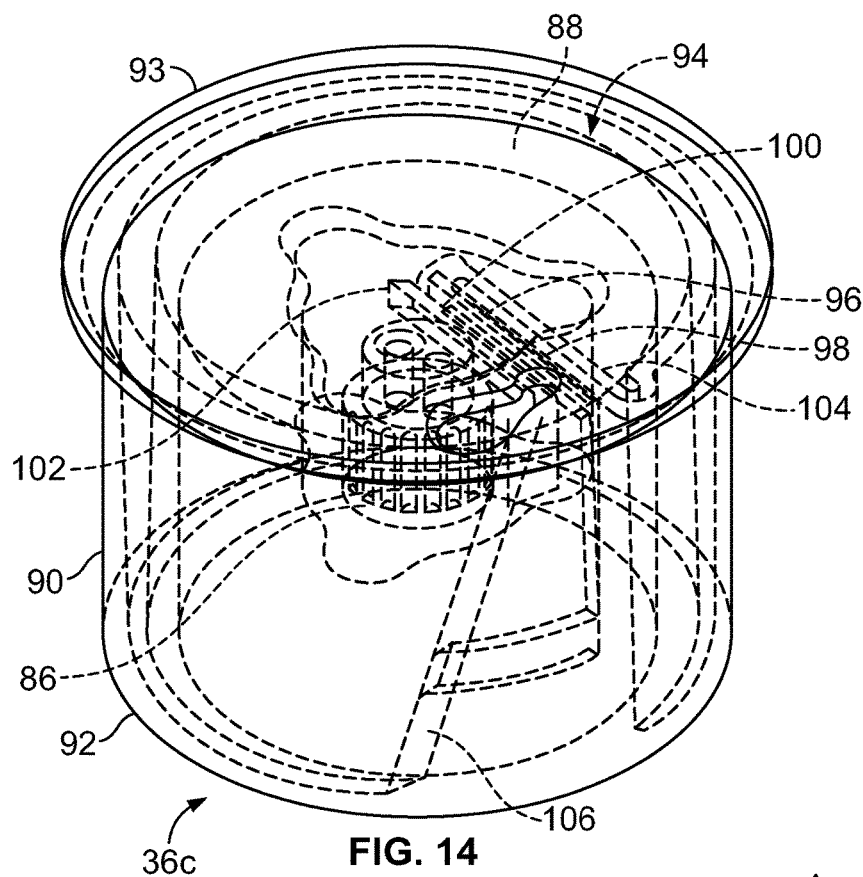
FIG. 14 is a perspective view of a third embodiment of a centrifugal separation chamber of a fluid flow circuit.
Figure 15:
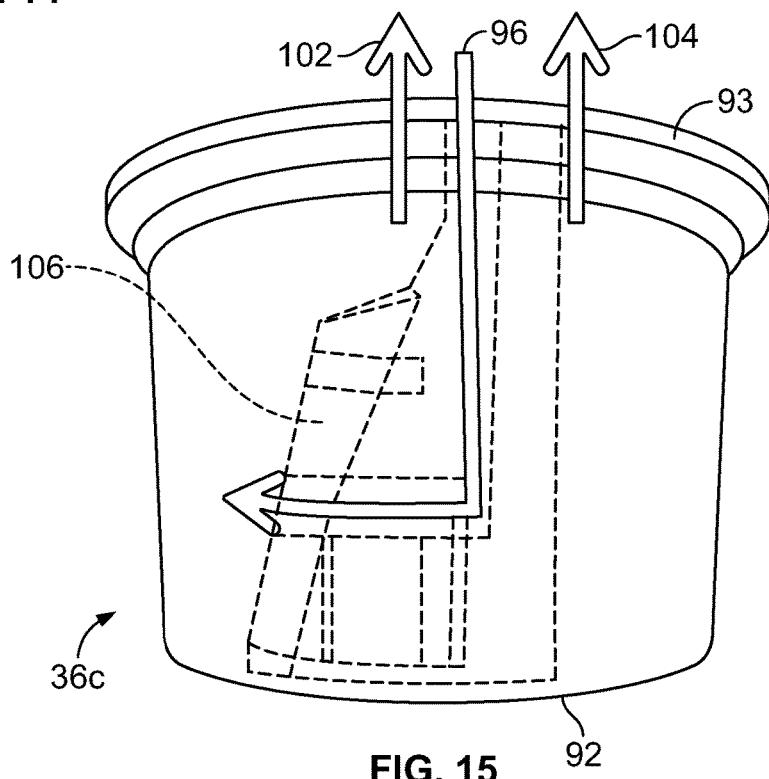
FIG. 15 is a front elevational view of the centrifugal separation chamber of FIG. 14.

FIGS. 14 and 15 show another exemplary embodiment of a centrifugal separation chamber 36c suitable for incorporation into a fluid flow circuit 12. The centrifugal separation chamber 36c is similar to the centrifugal separation chambers 36a and 36b of FIGS. 8 and 11 except for the location at which the inlet 96 opens into the channel 94. In contrast to the inlets 96 of the centrifugal separation chambers 36a and 36b of FIGS. 8 and 11, the inlet 96 of the centrifugal separation chamber 36c of FIG. 14 opens into the channel 94 at an intermediate axial location that is spaced from the first and second end wall portion 92 and 93 (while the outlets 102 and 104 open into the channel adjacent to the second end wall portion 93), as best shown in FIG. 15. The inlet 96 may open into the channel 94 at a location that is closer to the first end wall portion 92 than to the second end wall portion 93, at a location that is closer to the second end wall portion 93 than to the first end wall portion 92, or at a location that is equally spaced between the first and second end wall portions 92 and 93. The axial location at which the inlet 96 opens into the channel 94 may affect the separation of fluid within the channel 94, so the preferred location at which the inlet 96 opens into the channel 94 (which may also depend upon the nature of the fluid separation device paired with the centrifugal separation chamber 36c) may be experimentally determined.

1. Centrifugal Separation And Interface Detection Principles

Fluid flowed into the channel 94 separates into an optically dense layer RBC and a less optically dense layer PLS (FIGS. 16-18) as the centrifugal separation chamber 36 is rotated about the rotational axis 38. The optically dense layer RBC forms as larger and/or heavier fluid particles move under the influence of centrifugal force toward the outer (high-g) wall portion 90. If the fluid being separated is blood, the optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the optically dense layer RBC.

If the fluid being separated is blood, the less optically dense layer PLS typically includes a plasma constituent, such as platelet-rich plasma or platelet-poor plasma (and, hence, will be referred to herein as the "PLS layer"). Depending on the speed at which the centrifugal separation chamber 36 is rotated and the length of time that the blood is resident therein, other components (e.g., smaller white blood cells and anticoagulant) may also be present in the less optically dense layer PLS.

In one embodiment, blood introduced into the channel 94 via the inlet 96 will travel in a generally clockwise direction (in the orientation of FIG. 8) as the optically dense layer RBC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will re-suspend any platelets settled on the interface.

Figure 16:
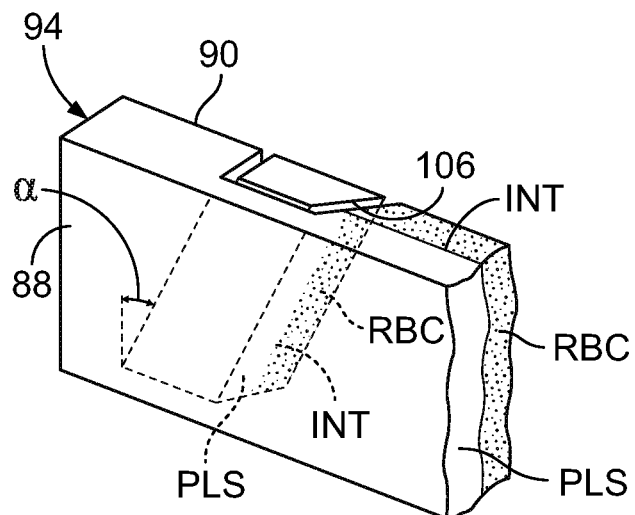
FIG. 16 is an enlarged perspective view of a portion of a channel of any of the centrifugal separation chambers of FIGS. 8-15, with an interface between separated fluid components being positioned at a (typically) desired location on a ramp defined within the channel.
Figure 17:
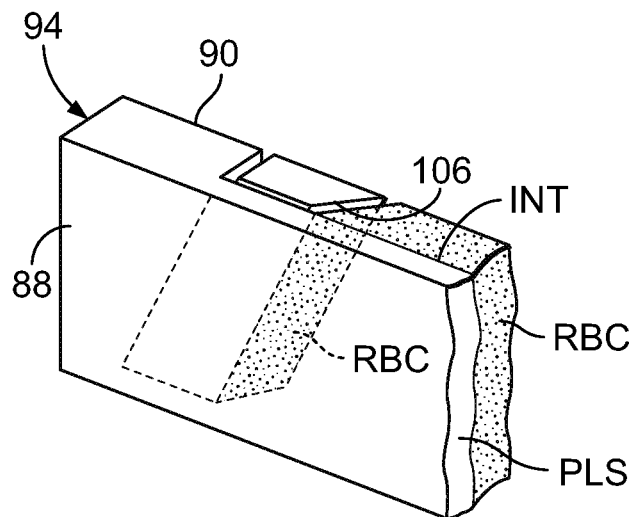
FIG. 17 is an enlarged perspective view of the channel and ramp of FIG. 16, with the interface being at a (typically) undesired high location on the ramp.
Figure 18:
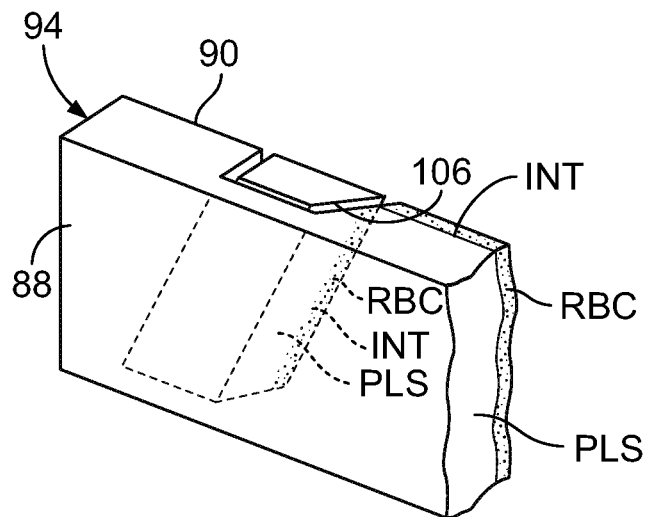
FIG. 18 is an enlarged perspective view of the channel and ramp of FIG. 16, with the interface being at a (typically) undesired low location on the ramp.

The transition between the optically dense layer RBC and the less optically dense layer PLS may be referred to as the interface INT. If the fluid being separated is blood, the interface INT contains mononuclear cells and peripheral blood stem cells. The location of the interface INT within the channel 94 of the centrifugal separation chamber 36 can dynamically shift during fluid processing, as FIGS. 16-18 show. If the location of the interface INT is too high (that is, if it is too close to the inner side wall portion 88 and the first outlet 102, as in FIG. 17), red blood cells can flow into the first outlet 102, potentially adversely affecting the quality of the low density components (platelet-rich plasma or platelet-poor plasma). On the other hand, if the location of the interface INT is too low (that is, if it resides too far away from the inner wall portion 88, as FIG. 18 shows), the collection efficiency of the system may be impaired. The ideal or target interface location may be experimentally determined, which may vary depending on any of a number of factors (e.g., the configuration of the centrifugal separation chamber 36, the rate at which the centrifugal separation chamber 36 is rotated about the rotational axis 38, etc.). As will be described herein, it may be advantageous to adjust the location of the interface INT away from the location of FIG. 16 during a separation procedure.

As described above, the fluid separation device 10 may include an interface monitoring system, a centrifuge outlet sensor M1, and a controller 18 with an interface control module to monitor and, as necessary, adjust or correct the position of the interface INT. In one embodiment, the centrifugal separation chamber 36 is formed with a ramp 106 extending from the high-g wall portion 90 at an angle α across at least a portion of the channel 94 (FIGS. 8 and 16-18). The angle α, measured with respect to the rotational axis 38 is about 25° in one embodiment. FIGS. 16-18 show the orientation of the ramp 106 when viewed from the low-g side wall portion 88 of the centrifugal separation chamber 36. Although it describes a flexible separation chamber, the general structure and function of the ramp 106 may be better understood with reference to U.S. Pat. No. 5,632,893, which is hereby incorporated herein by reference. The ramp 106 may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the optically dense layer RBC and the less optically dense layer PLS more discernible for detection, displaying the optically dense layer RBC, less optically dense layer PLS, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the light source 50 of the interface monitoring system is secured to a fixture or wall of the centrifuge compartment 32 and oriented to emit a light that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 88, as shown in FIGS. 5 and 6. The reflector may be a separate piece that is secured to the inner side wall portion 88 (e.g., by being bonded thereto) or may be integrally formed with the body of the centrifugal separation chamber 36.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 108 (FIGS. 7, 19, and 20), which is formed of a light-transmissive material (e.g., a clear plastic material) and has inner and outer walls 110 and 112 and first and second end walls 114 and 116 (FIG. 19). The inner wall 110 is positioned against the inner side wall portion 88 of the centrifugal separation chamber 36 and is oriented substantially perpendicular to the initial path of the light L from the light source 50. This allows light L from the light source 50 to enter into the prismatic reflector 108 via the inner wall 110 while continuing along its initial path. The light L continues through the prismatic reflector 108 along its initial path until it encounters the first end wall 114. The first end wall 114 is oriented at an angle (e.g., an approximately 45° angle) with respect to the first surface 110 and the second end wall 116, causing the light to be redirected within the prismatic reflector 108, rather than exiting the prismatic reflector 108 via the first end wall 114.

The first end wall 114 directs the light L at an angle to its initial path (which may be an approximately 90° angle, directing it from a path toward the rotational axis 38 to a path that is generally parallel to the rotational axis 38) toward the second end wall 116 (FIG. 20). The first end wall 114 and the inner and outer walls 110 and 112 of the prismatic reflector 108 may be configured to transmit the redirected light L from the first end wall 114 to the second end wall 116 by total internal reflection. The second end wall 116 is oriented substantially perpendicular to the redirected path of the light L through the prismatic reflector 108, such that the light L will exit the prismatic reflector 108 via the second end wall 116, continuing along its redirected path. In one embodiment, the second end wall 116 is roughened or textured or otherwise treated or conditioned to diffuse the light L as it exits the prismatic reflector 108, which may better ensure that the light L reaches the light detector 52 (FIG. 7).

Figure 21:
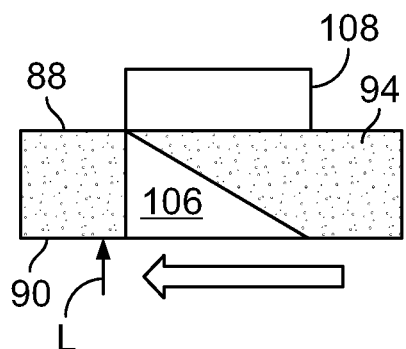
FIGS. 21-24 are diagrammatic views of the ramp and prismatic reflector of the centrifugal separation chamber passing through the path of light from the light source during a calibration phase.
Figure 25:
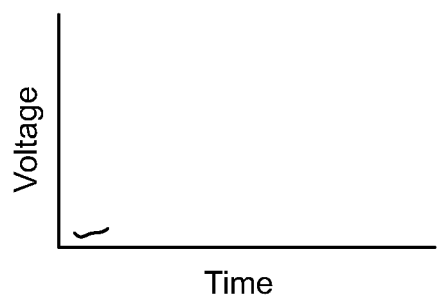
FIGS. 25-28 are diagrammatic views of the voltage output or signal transmitted by the light detector during the conditions shown in FIGS. 21-24, respectively.
Figure 22:
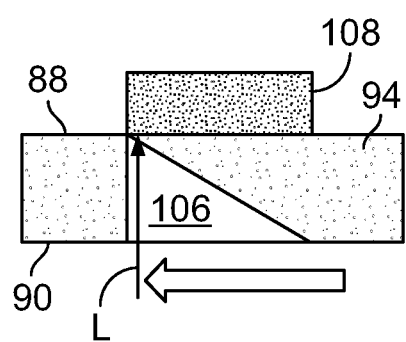

The prismatic reflector 108 may be angularly aligned with the ramp 106, such that the light L from the light source 50 will only enter into the prismatic reflector 108 when the ramp 106 has been rotated into the path of the light L. At all other times (when the ramp 106 is not in the path of the light L), the light L will not reach the prismatic reflector 108 and, thus, will not reach the light detector 52. This is illustrated in FIGS. 21-24, which show the ramp 106 and prismatic reflector 108 as the centrifugal separation chamber 36 is rotated about the rotational axis 38 (while the light source 50 remains in a fixed location). In FIG. 21, the ramp 106 and prismatic reflector 108 have not yet been rotated into the initial path of the light L from the light source 50. At this time, no light is transmitted to the light detector 52, such that the output voltage of the light detector 52 (i.e., the signal transmitted from the light detector 52 to the controller 18) is in a low- or zero-state (FIG. 25).

Figure 26:
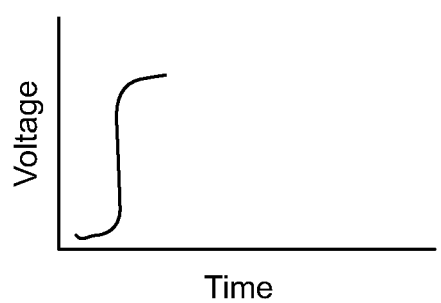

Upon the ramp 106 first being rotated into the initial path of the light L from the light source 50 (FIG. 22), the light L will begin to reach the prismatic reflector 108, which directs the light L to the light detector 52. This causes the voltage output of the light detector 52 (i.e., the signal transmitted from the light detector 52 to the controller 18) to increase to a non-zero value or state, as shown in FIG. 26.

Figure 23:
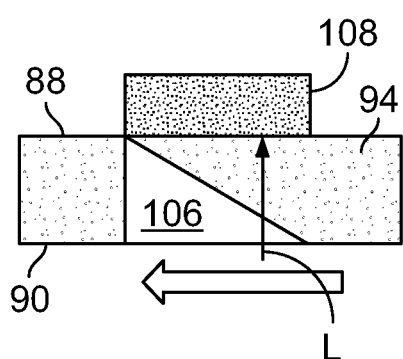
Figure 27:
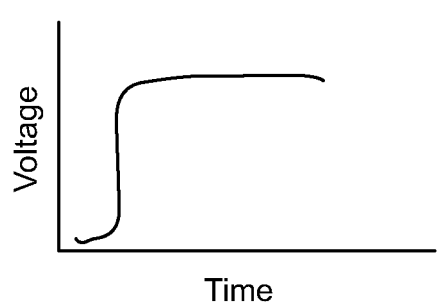
Figure 24:
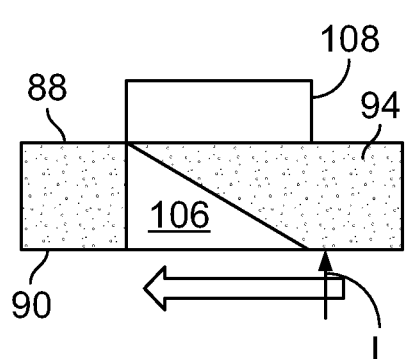

During a calibration phase, the channel 94 is filled with a fluid that will transmit the light L rather than absorbing or reflecting the light or otherwise preventing the light L from reaching the prismatic reflector 108, such that the voltage output of the light detector 52 will remain generally constant as the ramp 106 and prismatic reflector 108 are rotated through the initial path of the light L from the light source 50 (FIGS. 23 and 27). Such a calibration phase may coincide with a priming phase during which saline is pumped through the fluid flow circuit 12 to prime the fluid flow circuit 12 or may comprise a separate phase. A calibration phase may be useful in ensuring the proper operation of the light source 50 and the light detector 52, standardizing the readings taken during a separation procedure in case of any irregularities or imperfections of the centrifugal separation chamber 36, and establishing a baseline value for the signal transmitted from the light detector 52 to the controller 18 when the ramp 106 and prismatic reflector 108 are aligned with the light source 50. As will be described in greater detail, the voltage output of the light detector 52 will typically not remain constant as the ramp 106 and prismatic reflector 108 are rotated through the initial path of the light L from the light source 50 because the different fluid layers displayed on the ramp 106 will allow different amounts of light L to reach the prismatic reflector 108.

Figure 28:
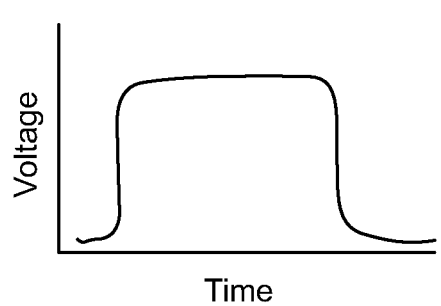

The ramp 106 and prismatic reflector 108 are eventually rotated out of alignment with the light source 50 (FIG. 24), at which time no light L will reach the prismatic reflector 108 and the voltage output of the light detector 52 will return to its low- or zero-state (FIG. 28).

It may be advantageous for the light L to have a relatively small diameter for improved resolution of the signal that is generated by the light detector 52.

2. Exemplary Interface Detection and Correction Procedure

During separation of blood within the channel 94, the light L from the light source 50 travels through a light-transmissive portion of the outer side wall portion 90 and the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion not absorbed or reflected by the fluids) exits the channel 94 by striking and entering a light-transmissive portion of the inner side wall portion 88. The light L passes through the inner side wall portion 88 and enters the prismatic reflector 108, which redirects the light L from its initial path to the light detector 50, as described above. Thus, it will be seen that the light L reaches the light detector 52 after intersecting and traveling through the separated blood components in the channel 94 only once, in contrast to known systems in which light from a light source travels through a ramp and a fluid-filled channel before being reflected back through the channel to reach a light detector. Requiring the light L to traverse the fluid-filled channel 94 only once before reaching the light detector 52 instead of twice may be advantageous in that it tends to increase the intensity of the light L that reaches the light detector 52, which may improve monitoring and correction of the interface location.

The light detector 52 generates a signal that is transmitted to the interface control module of the controller 18, which can determine the location of the interface INT on the ramp 106. In one embodiment, the location of the interface INT is associated with a change in the amount of light L that is transmitted through the less optically dense layer PLS and the optically dense layer RBC. For example, the light source 50 may be configured to emit a light L that is more readily transmitted by platelet-rich plasma or platelet-poor plasma than by red blood cells, such as red visible light (from a laser or a differently configured light source 50), which is substantially absorbed by red blood cells. The less optically dense layer PLS and the optically dense layer RBC each occupy a certain portion of the ramp 106, with the light detector 52 receiving different amounts of light L depending on whether the light L travels through the less optically dense layer PLS on the ramp 106 or the optically dense layer RBC on the ramp 106. The percentage of the ramp 106 occupied by each layer is related to the location of the interface INT in the channel 94. Thus, by measuring the amount of time that the voltage output or signal from the light detector 52 is relatively high (corresponding to the time during which the light L is passing through only the less optically dense layer PLS on the ramp 106), the controller 18 may determine the location of the interface INT and take steps to correct the location of the interface INT, if necessary.

FIGS. 29-32 show a portion of the ramp 106 being rotated into and through the initial path of the light L from the light source 50. Four specific events are shown: just before the ramp 106 is rotated into the path of the light L (FIG. 29), the ramp 106 first being rotated into the path of the light L (FIG. 30), just before the interface INT displayed on the ramp 106 is rotated into the path of the light L (FIG. 31), and just after the interface INT is rotated into the path of the light L (FIG. 32). FIGS. 33-36 respectively illustrate the voltage output of the light detector 52 (corresponding to the signal that it transmits to the controller 18) during each of these events.

As described above, the light detector 52 will receive no light L from the light source 50 when the prismatic reflector 108 is out of alignment with the initial path of the light L from the light source 50, as shown in FIG. 29. FIG. 33 shows that the output voltage of the light detector 52 (i.e., the signal transmitted from the light detector 52) to the controller 18) at this time is in a low- or zero-state.

When the ramp 106 is first rotated into the path of light L from the light source 50 (FIG. 30), the light detector 52 may begin receiving light L. The amount of light L received by the light detector 52 depends upon the fluid on the ramp 106 encountered by the light L (i.e., the fluid in the channel 94 between the ramp 106 and the inner side wall portion 88 that the light L must traverse before being directed to the light detector 52). As described above, the less optically dense layer PLS occupies a certain percentage of the channel 94 adjacent to the inner side wall portion 88, while the optically dense layer RBC occupies a certain percentage of the channel 94 adjacent to the outer side wall portion 90 (with the interface INT positioned at the transition between the two separated blood component layers). The illustrated ramp 106 is closest to the inner side wall portion 88 at its left end (in the orientation of FIGS. 29-32), while being farther spaced from the inner side wall portion 88 at its right end. At and adjacent to its left end, the ramp 106 will display only the fluid positioned closest to the inner side wall portion 88 (i.e., the less optically dense layer PLS), while the ramp 106 will display only the fluid positioned closest to the outer side wall portion 90 (i.e., the optically dense layer RBC) at and adjacent to its right end, as shown in FIGS. 29-32. At some point between its ends, the angled ramp 106 will be at a radial position where it will display the transition between the less optically dense layer PLS and the optically dense layer RBC (i.e., the interface INT). Hence, the location of the interface INT on the ramp 106 is dependent upon the percentage of the width of the ramp 106 that displays the less optically dense layer PLS (which is indicative of the percentage of the channel 94 occupied by the less optically dense layer PLS) and the percentage of the width of the ramp 106 that displays the optically dense layer RBC (which is indicative of the percentage of the channel 94 occupied by the optically dense layer RBC). It should be understood that the percentage of the ramp 106 occupied by the less optically dense layer PLS and by the optically dense layer RBC is not necessarily equal to the percentage of the channel 94 occupied by the less optically dense layer PLS and by the optically dense layer RBC, but that the percentage of the ramp 106 occupied by a separated blood component layer may be merely indicative of the percentage of the channel 94 occupied by that separated fluid component layer.

In such an embodiment, as the ramp 106 is rotated into the path of the light L from the light source 50, the light L will first encounter the portion of the ramp 106 that is positioned closest to the inner side wall portion 88 (i.e., the section of the ramp 106 that most restricts the channel 94), as shown in FIG. 30. As described above, the less optically dense layer PLS will be positioned adjacent to the inner side wall portion 88 as it separates from the optically dense layer RBC, such that the fluid displayed on this radially innermost section of the ramp 106 (i.e., the fluid present in the channel 94 between the ramp 106 and the inner side wall portion 88) will be the less optically dense layer PLS. The light is substantially transmitted through the less optically dense layer PLS to the inner side wall portion 88, and through the light-transmissive inner side wall portion 88 to the prismatic reflector 108, which redirects the light L to the light detector 52. This causes the voltage output of the light detector 52 (i.e., the signal transmitted from the light detector 52 to the controller 18) to increase to a non-zero value or state, as shown in FIG. 34. Depending on the nature of the light L, the amount of light L received by the light detector 52 (and, hence, the magnitude of the voltage output) after the light L has passed through the less optically dense layer PLS may be greater than, less than, or equal to the amount of light L received by the light detector 52 after passing through saline during the calibration phase described above.

Further rotation of the ramp 106 through the path of light L from the light source 50 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L (as shown in FIG. 31), the only fluid in the channel 94 that the light L will have passed through will be the less optically dense layer PLS, such that a generally uniform level of light reaches the light detector 52 between the conditions shown in FIGS. 30 and 31. Accordingly, the voltage output of the light detector 52 will be generally uniform (at an elevated level) the whole time that the ramp 106 passes through the path of the light L before being exposed to the interface INT, as shown in FIG. 35. The controller 18 may be programmed and/or configured to consider a signal that deviates from a maximum signal level (e.g., a 10% decrease) to be part of the elevated signal for purposes of calculating the pulse width of the signal. The controller 18 will treat a greater deviation (i.e., a greater decrease in the magnitude of the signal) as the end of the elevated signal for purposes of calculating the pulse width of the signal.

Just after the interface INT has been rotated into the path of light L from the light source 50, the light L will begin to encounter the optically dense layer RBC in the channel 94, as shown in FIG. 32). As described above, the optically dense layer RBC will be positioned adjacent to the outer side wall portion 90 as it separates from the less optically dense layer PLS, such that the optically dense layer RBC will not be displayed on the ramp 106 until the ramp 106 is spaced a greater distance away from the inner side wall portion 88 (i.e., toward the right end of the ramp 106 in the orientation of FIGS. 29-32). Less light L is transmitted through the optically dense layer RBC than through the less optically dense layer PLS (which may include all or substantially all of the light L being absorbed by the optically dense layer RBC), such that the amount of light L that reaches the light detector 52 will decrease compared to the amount of light L that reaches the light detector 52 while traveling through only the less optically dense layer PLS in the channel 94 (FIGS. 30 and 31).

When receiving less light L, the voltage output or signal from the light detector 52 will decrease to a lower level than when the light L was passing through only the less optically dense layer PLS in the channel 94, as shown in FIG. 36. When the light L encounters the optically dense layer RBC in the channel 94, the light detector 52 may be generating a signal or voltage output that is approximately equal to its zero-state (as in FIG. 33, when the light detector 52 is receiving no light L) or a signal or voltage output that is some degree less than the magnitude of the signal or voltage output generated while the light L encounters only the less optically dense layer PLS in the channel 94. The controller 18 may be programmed and/or configured to recognize this lower level signal as representing the presence of the optically dense layer RBC on the ramp 106 (and in the portion of the channel 94 being traversed by the light L) and treat this lower level signal as the end point of the elevated signal generated by the light detector 52 while light L passes through only the less optically dense layer PLS in the channel 94.

Figure 37:
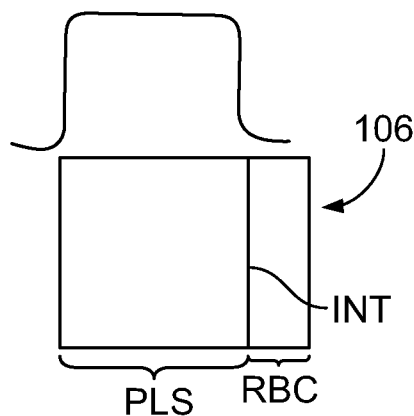
FIGS. 37 and 38 are diagrammatic views of separated fluid components on the ramp and the pulse widths of a signal generated by the light detector for each condition.
Figure 38:
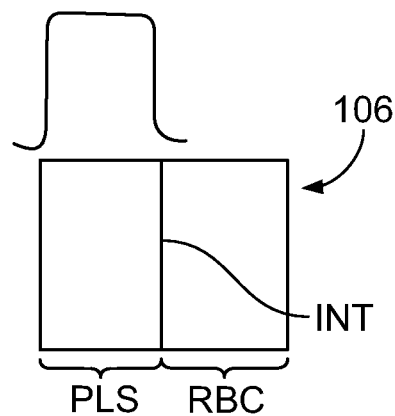
Figure 39:
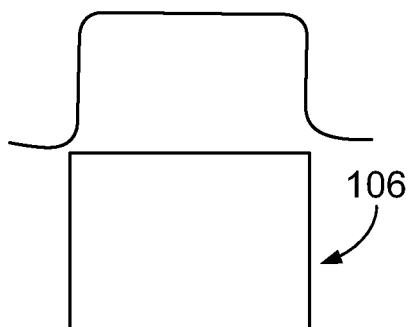
FIG. 39 is a diagrammatic view of saline on the ramp and the pulse width of a signal generated by the light detector for such a condition.

Thus, the pulse width of the elevated signal from the light detector 52 to the controller 18 (i.e., the time during which light L is traversing only the less optically dense layer PLS in the channel 94) is determined by the percentages of the ramp 106 that are occupied by the less optically dense layer PLS and the optically dense layer RBC. Accordingly, a greater pulse width of the signal from the light detector 52 to the controller 18 is associated with the less optically dense layer PLS occupying a larger portion of the ramp 106 (as shown in FIG. 37 from the point of view of the light source 50, which may correspond to the condition shown in FIG. 17) and will be indicative of a thinner optically dense layer RBC on the ramp 106 (and in the channel 94). Conversely, a signal from the light detector 52 to the controller 18 having a narrower pulse width is associated with the less optically dense layer PLS occupying a smaller portion of the ramp 106 (as shown in FIG. 38) and will be indicative of a thicker optically dense layer RBC on the ramp 106 (and in the channel 94).

The controller 18 may compare the pulse width of the signal to the pulse width generated during the calibration phase (described above and shown in FIG. 39), which corresponds to the pulse width when light L is transmitted to the light detector 52 over the entire width of the ramp 106. The pulse width of the signal generated by the light detector 52 during the calibration phase may be referred to as the saline calibration signal. Comparing these two pulse widths will indicate the percentage of the ramp 106 that is occupied by the less optically dense layer PLS and by the optically dense layer RBC, which information the controller 18 may use to determine the location of the interface INT within the channel 94. In particular, the interface position may be calculated as follows:

Interface position (%)=((saline calibration pulse width−current plasma pulse width)/saline calibration pulse width)*100  [Equation 1]

It will be seen that Equation 1 effectively calculates the percentage of the ramp 106 that is occupied by the optically dense layer RBC, as the difference between the two pulse widths corresponds to the length of time that the ramp 106 is rotated through the path of the light L without the light detector 52 received an elevated level of light L (i.e., the amount of time that the ramp 106 is rotated through the path of the light L while the optically dense layer RBC is present on the ramp 106).

Figure 40:
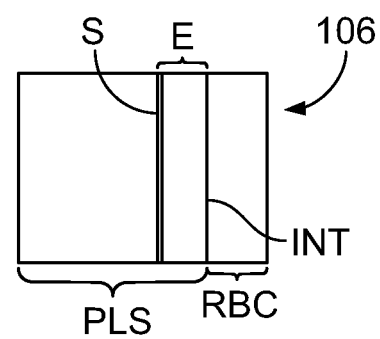
FIG. 40 is a diagrammatic view of the position of an interface between separated fluid components on the ramp compared to a target interface location.

When the location of the interface INT on the ramp 106 has been determined, the interface control module compares the actual interface location with a desired interface location, which may be referred to as the setpoint S. The difference between the setpoint S and the calculated interface position may be referred to as the error signal E, which is shown in FIG. 40. It should be understood that so expressing the error signal E in terms of a targeted red blood cell percentage value (i.e., the percentage of the ramp 106 that is actually occupied by the optically dense layer RBC vs. the percentage of the ramp 106 which should be occupied by the optically dense layer RBC) is merely exemplary, and that the error signal E may be expressed or calculated in any of a number of other ways.

When the control value is expressed in terms of a targeted red blood cell percentage value, a negative error signal E indicates that the optically dense layer RBC on the ramp 106 is too large (as FIG. 17 shows). The interface control module of the controller 18 generates a signal to adjust an operational parameter accordingly, such as by reducing the rate at which the less optically dense layer PLS is removed through the first outlet 102 under action of a pump of the blood separation device 10. The interface INT moves toward the desired control position (as FIG. 16 shows), where the error signal is zero.

A positive error signal indicates that the optically dense layer RBC on the ramp 106 is too small (as FIGS. 18 and 40 show). The interface control module of the controller 18 generates a signal to adjust an operational parameter accordingly, such as by increasing the rate at which the less optically dense layer PLS is removed through the first outlet 102 under action of a pump of the fluid separation device 10. The interface INT moves toward the desired control position (FIG. 16), where the error signal is again zero.

It should be understood that this system for controlling the location of the interface INT is merely exemplary and that differently configured and/or functioning systems may be employed without departing from the scope of the present disclosure.

3. Adjustment of Target Interface Location

The foregoing description relates to determination of the location of an interface INT and adjustment of the location of the interface INT to move it to a target interface location or setpoint S. However, according to an aspect of the present disclosure, the target interface location or setpoint S is not necessarily static throughout a separation procedure, but may be adjusted to a different target location during a procedure. For example, if a first separated fluid component evidences the presence of a second separated fluid component (e.g., if red blood cells are detected in platelet-rich plasma), it may be advantageous to move the setpoint during the procedure from the current target location to an adjusted target location that tends to reduce the likelihood that an additional amount of the second separated fluid component is added to the first separated fluid component. In another example, if a separated fluid component does not have a desired composition (e.g., if the platelet concentration of platelet-rich plasma separated from anticoagulated whole blood is lower than desired), it may be advantageous to move the setpoint during the procedure from the current target location to an adjusted target location that tends to promote a more desirable composition.

Figure 41:
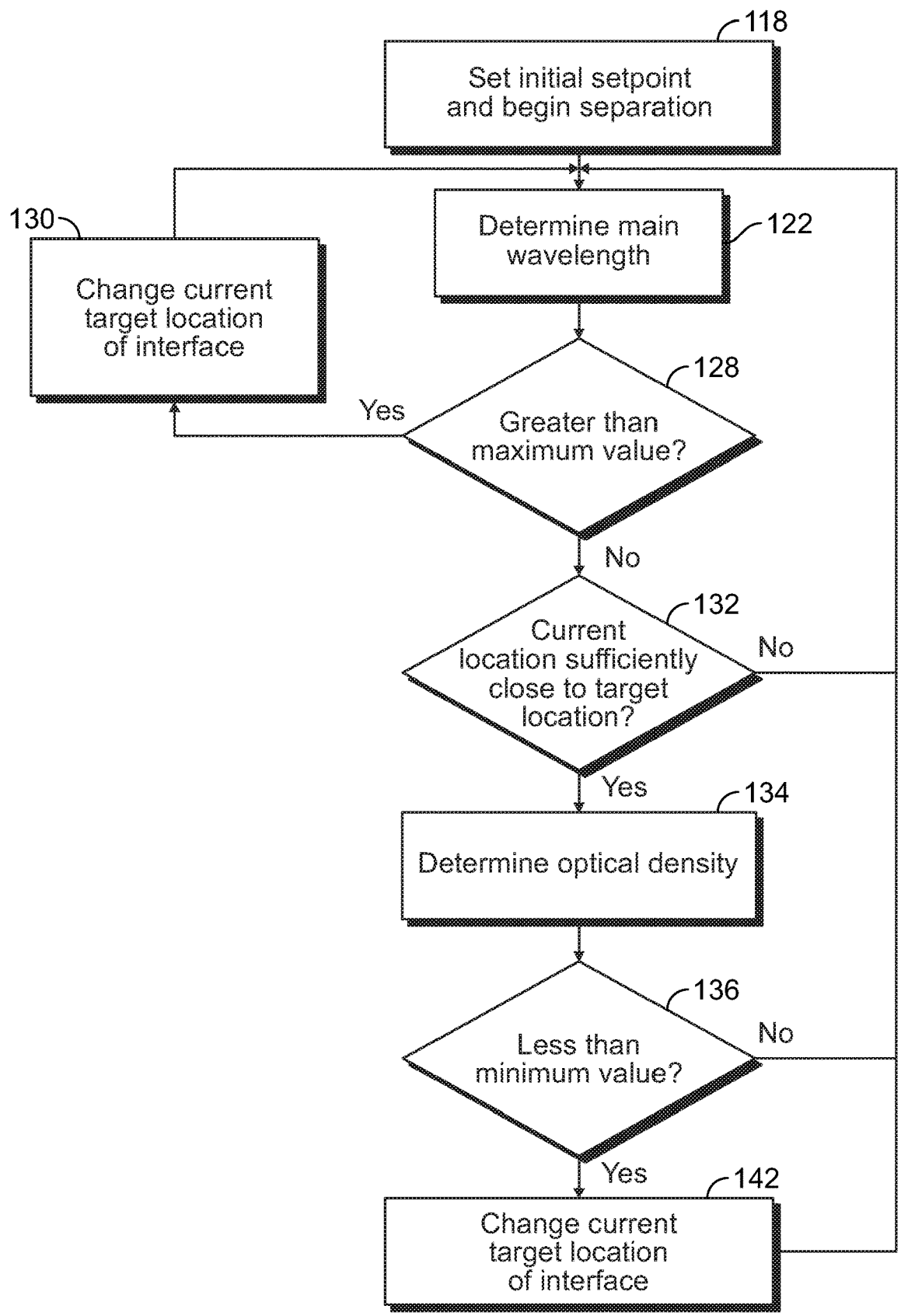
FIG. 41 illustrates an exemplary approach to mid-procedure adjustment of a target interface position based on the color and optical density of a separated fluid component.

FIG. 41 shows an exemplary approach to mid-procedure adjustment of the setpoint. A separation procedure begins with fluid being conveyed into the centrifugal separation chamber 36 of a fluid flow circuit 12 positioned within the centrifuge or centrifugal separator 16. The fluid is separated into at least two fluid components, with the separated fluid components continuously flowing through the centrifugal separation chamber 36, with an interface positioned therebetween. The separation procedure begins with an initial setpoint or target location of the interface, as generally identified at 118 in FIG. 41. The initial target location may be experimentally determined and based on the separation procedure selected by an operator or may be otherwise selected or determined. For example, in the case of a blood separation procedure in which red blood cells (as an optically dense layer RBC) are separated from platelet-rich plasma (as a less optically dense layer PLS), the initial target location of the interface may be the location at which the platelet concentration of the platelet-rich plasma will be sufficiently high without red blood cells tending to exit the centrifugal separator 16 with the platelet-rich plasma.

The separated fluid components flow out of the centrifugal separation chamber 36, with at least a portion of one of the separated fluid components eventually flowing through a vessel 120 of the fluid flow circuit 12 (FIG. 2). The vessel 120 is shown in FIG. 2 as being in fluid communication with the centrifugal separation chamber 36, without necessarily being directly connected to the centrifugal separation chamber 36, though it should be understood that it is within the scope of the present disclosure for the vessel 120 to be directly connected to the centrifugal separation chamber 36. It should also be understood that the nature and configuration of the vessel 120 may vary without departing from the scope of the present disclosure, for example with the vessel 120 being configured as a flexible tubing or as a cavity defined in a cassette 48 of the fluid flow circuit 12.

The separated fluid component flowing through the vessel 120 is monitored to determine a main or dominant wavelength of light reflected off of the separated fluid component, as generally identified at 122 in FIG. 41. This may be achieved by the centrifuge outlet sensor M1 working in combination with the controller 18, and determines the color of the separated fluid component. In the case of platelet-rich plasma flowing through the vessel 120, this amounts to determining the redness of the platelet-rich plasma, which is an indication of the amount of red blood cells in the platelet-rich plasma.

The main wavelength of the separated fluid component in the vessel 120 may be determined by any suitable approach without departing from the scope of the present disclosure. In one embodiment, the main wavelength of the separated fluid component in the vessel 120 is determined according to the approach described in U.S. patent application Ser. No. 16/382,261, filed Apr. 12, 2019, which is hereby incorporated herein by reference. According to such an approach, the centrifuge outlet sensor M1 is configured as a colorimetric optical sensor, which is provided with a broadband light source 124 configured to expose the vessel 120 to broadband light B so as to cause an amount of the light to be reflected by the separated fluid component in the vessel 120 and received by a light detector or optical spectrometer 126 of the centrifuge outlet sensor M1 as reflected light R, as in FIG. 42. In an exemplary embodiment, the broadband light source 124 is configured to emit a light B including at least all wavelengths in the visible range (from approximately 400 nm to approximately 700 nm), but may also include wavelengths above and/or below the visible range.

Figure 42:
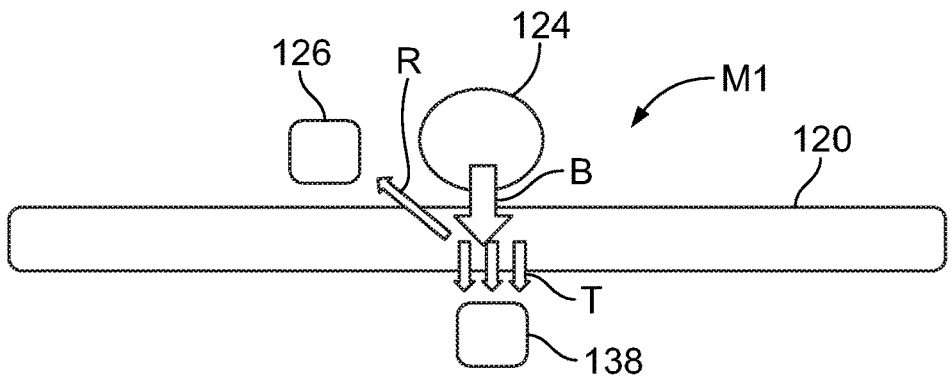
FIG. 42 is a diagrammatic view of an exemplary configuration of a centrifuge outlet sensor having a single light source.
Figure 43:
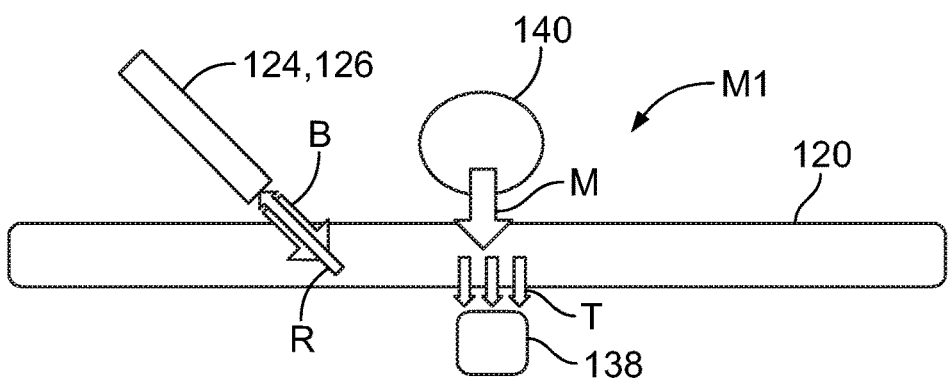
FIG. 43 is a diagrammatic view of an exemplary configuration of a centrifuge outlet sensor having two light sources.
Figure 44:
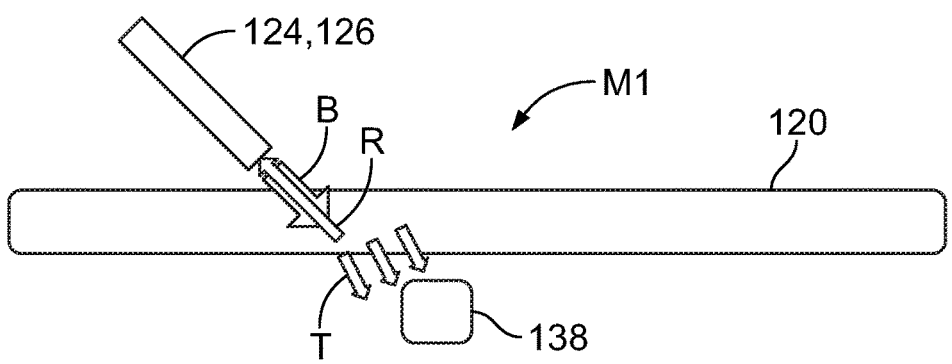
FIG. 44 is a diagrammatic view of another exemplary configuration of a centrifuge outlet sensor having a single light source.

In the embodiment of FIG. 42, the broadband light source 124 emits light B in a direction that is substantially perpendicular to a direction in which the separated fluid component flows through the vessel 120, but in other embodiments (as shown in FIGS. 43 and 44) the broadband light source 124 may be configured to emit light B in a direction that causes the light B to strike a surface of the vessel 120 at an angle. The angle may vary, for example, with the angle being in the range of 30-60°, with the angle being approximately 45° in one embodiment.

Regardless of the position of the broadband light source 124, the portion of the light B that is not reflected off of the surface of the vessel 120 will be transmitted through the surface and into the vessel 120, wherein it will be absorbed and scattered based on the unique properties of the separated fluid component within the vessel 120. The portion of the light reflected back out of the vessel 120 is received by the light detector 126 as reflected light R. The light detector 126 may be oriented to receive reflected light R traveling at an angle with respect to the direction in which the separated fluid component is flowing through the vessel 120, as shown in the embodiments of FIGS. 42-44. Orienting the light detector 126 at an angle that is different from the angle of reflection of light reflected off of the surface of the vessel 120 (specular reflection) will reduce the amount of that light that is received by the light detector 120. This increases the ratio of light R reflected from the separated fluid component (which may be used to determine characteristics of the separated fluid component) to the light reflected off of the surface of the vessel 120 (which does not contain any information regarding the separated fluid component) that is received by the light detector 126. In the embodiment of FIG. 42, the light B is emitted from a location positioned downstream of the light detector 126, though it should be understood that the light B may instead be emitted from a position upstream of the light detector 126. In the embodiments of FIGS. 43 and 44, the broadband light B is shown as being emitted from substantially the same position at which the reflected light R is received. This may be achieved (for example) by the use of an optical fiber bundle, with at least one transmitting optical fiber that directs broadband light B from a broadband light source 124 toward the vessel 120 and at least one receiving optical fiber that receives the reflected light R and directs it to the light detector 126.

The light detector 126 may be configured for measurement and wavelength differentiation of at least a portion of the reflected light R that it receives or it may instead pass a signal along to the controller 18, with the controller 18 measuring and differentiating wavelengths of the reflected light R. In one embodiment, the light detector 126 is provided as a compact CCD spectrometer capable of measuring the intensity of light at each wavelength in the range of 200 nm-1000 nm of the type marketed by Thorlabs, Inc. of Newton, N.J., but it may also be differently configured without departing from the scope of the present disclosure.

The reflected light R is analyzed to differentiate the wavelengths contained within the light R to produce an optical spectrum of the light R, which indicates the intensity of the light R at different wavelengths. The main wavelength is then determined from the optical spectrum, such as by using a color specification system, which may be incorporated into the controller 18.

Once the main wavelength of the reflected light R has been determined, it is compared to a maximum wavelength value, as generally identified in FIG. 41 at 128. The maximum wavelength value may represent an undesirable condition of the separated fluid component in the vessel 120. For example, in the case of platelet-rich plasma, as described above, the main wavelength of the reflected light R will be an indication of the redness of the platelet-rich plasma in the vessel 120, which reflects the amount of red blood cells in the platelet-rich plasma. The greater the amount of red blood cells in the platelet-rich plasma, the more red the platelet-rich plasma will be and the higher the main wavelength of the reflected light R will be. The maximum wavelength value may, thus, be a wavelength that indicates a particular amount of red blood cells in the platelet-rich plasma. If the main wavelength of the reflected light R is greater than the maximum wavelength value, it is an indication that too many red blood cells are being removed from the centrifugal separation chamber 36 with the platelet-rich plasma. On the other hand, if the main wavelength of the reflected light R is not greater than the maximum wavelength value, it is an indication that the amount of red blood cells in the platelet-rich plasma is less than a preselected or predetermined amount that is considered to be unacceptable. In a particular example, the main wavelength value may be 590 nm, as it has been determined that platelet-rich plasma free of red blood cells will have a main wavelength in the range of 585-590 nm. Other main wavelength values may also be employed, particularly if some other fluid is being separated and some other condition is being monitored for by the centrifuge outlet sensor M1.

When it has been determined that the main wavelength of the reflected light R is greater than the maximum wavelength value, as generally identified at 130 in FIG. 41, the controller 18 may change the current target location of the interface to a main wavelength-adjusted target location that becomes the new current target location of the interface (replacing the initial target location or any other previously defined current target location). The main wavelength-adjusted target location may be anything different from the current target location of the interface, but is preferably a location that tends to reduce the condition represented by the elevated main wavelength of the reflected light R. In the case of platelet-rich plasma, the main wavelength-adjusted target location may be farther from the low-G wall of the centrifuge 16 or centrifugal separation chamber 36 than the current location of the interface (not the current target location of the interface). Causing the interface to move from its current location toward a more radially outward position will move the red blood cells away from the first outlet 102 of the centrifugal separation chamber 36, thereby reducing the amount of red blood cells that will exit the centrifugal separation chamber 36 with the platelet-rich plasma and also reducing the main wavelength of the broadband light reflected off of the platelet-rich plasma in the vessel 120.

As described above, the position of the interface may be expressed in terms of the percentage of ramp 106 occupied by the optically dense layer RBC, with a greater percentage equating to a position that is closer to the low-G wall of the centrifuge 16 or centrifugal separation chamber 36. Thus, in one embodiment, the main wavelength-adjusted target location may represent a preselected or predetermined change in the percentage of the ramp 106 currently occupied by the optically dense layer RBC. In an exemplary embodiment, the main wavelength-adjusted target location is determined by setting the current target location of the interface to a location corresponding to a 2% reduction in the percentage of the ramp 106 occupied by the optically dense layer RBC compared to the current percentage of the ramp 106 occupied by the optically dense layer RBC. In an example, the initial (and current) target location of the interface may correspond to 45% of the ramp 106 being occupied by the optically dense layer RBC. If, at a current interface location corresponding to 40% of the ramp 106 being occupied by the optically dense layer RBC, it is determined that the main wavelength of light reflected off of the separated fluid component in the vessel 120 is greater than the maximum wavelength value, the controller 18 may change the current target location of the interface to a main wavelength-adjusted target location or new current target location of the interface corresponding to 38% of the ramp 106 being occupied by the optically dense layer RBC (i.e., 2% less than the current interface location).

After adjusting the current target location of the interface, the main wavelength of the reflected light R may be determined again and compared to the maximum wavelength value (as in steps 122 and 128), with the current target location of the interface again being adjusted if the main wavelength is still greater than the maximum wavelength value. This cycle may be repeated until the main wavelength of the reflected light R is not greater than the maximum wavelength value, at which time the current target location of the interface is kept the same (i.e., without it being adjusted based on the main wavelength of the reflected light R) and the controller 18 moves to the next step.

When the main wavelength of the reflected light is sufficiently low, the current interface position is compared to the current target location of the interface, as generally indicated at 132 in FIG. 41. If the position of the interface is not sufficiently close to the current target location, then the above-described steps may be repeated until the interface is at or sufficiently close to the current target location. In an exemplary embodiment, the controller 18 determines whether the current location of the interface corresponds to the ramp 106 being occupied by a percentage of the optically dense layer RBC that is within 0.5% of the percentage of the ramp 106 occupied by the optically dense layer RBC at the current target location of the interface. For example, if the current target location of the interface corresponds to 38% of the ramp 106 being occupied by the optically dense layer RBC, then the controller 18 determines whether the optically dense layer RBC occupies between 37.5% and 38.5% of the ramp 106. As will be described in greater detail, in the next steps (generally indicated at 134 and 136 in FIG. 41), the optical density of the separated fluid component in the vessel 120 is considered. If the interface is not sufficiently close to the current target location, it is assumed that the system is not operating at the setpoint S, such that it may be premature to consider the optical density of the separated fluid component in the vessel 120 (due to the optical density likely being too low if operating below the setpoint S and too high if operating above the setpoint S).

When it has been determined that the position of the interface is sufficiently close to the current target location or setpoint S, the optical density of the separated fluid component in the vessel 120 is determined, as generally identified at 134 in FIG. 41. The optical density of the separated fluid component in the vessel 120 may be determined by any suitable approach without departing from the scope of the present disclosure. In one embodiment, the optical density of the separated fluid component in the vessel 120 is determined according to the approach described in PCT Patent Application Publication No. WO 99/03557, which is hereby incorporated herein by reference. According to such an approach, the centrifuge outlet sensor M1 includes a second light detector 138 (FIGS. 42-44). Light having a wavelength that is absorbed or scattered by a constituent of the separated fluid component is directed through the vessel 120 and the separated fluid component in the vessel 120. An amount of the light is transmitted through the vessel 120 and the separated fluid component and is received by the second light detector 138 as transmitted light T. The percentage of the light that is transmitted through the vessel 120 and received by the second light detector 138 (compared to a 100% transmission baseline) is indicative of the concentration of the constituent in the separated fluid component in the vessel 120. Thus, if the concentration of the constituent in the separated fluid component in the vessel 120 is relatively high, then a lesser amount of transmitted light will be received by the second light detector 138 and the weaker the signal that will be transmitted to the controller 18 by the second light detector 138 (corresponding to a greater optical density).

In the embodiment of FIG. 42, the broadband light source 124 of the centrifuge outlet sensor M1 emits light B having a suitable wavelength or wavelengths among the multiple wavelengths or within the range of wavelengths of the light B, with a portion of the light being reflected and received by the first light detector 126 as reflected light R (to determine the color of the separated fluid component in the vessel 120) and another portion of the same light being transmitted through the vessel 120 and received by the second light detector 138 as transmitted light T (to determine the optical density of the separated fluid component in the vessel 120). This is also the case in the embodiment of FIG. 44. However, in the embodiment of FIG. 43, a second light source 140 is provided, with the second light source 140 configured to emit light M having a single wavelength suitable for determining the optical density of the separated fluid component in the vessel 120, rather than being a broadband light source. In addition to being configured to emit different types of light, the two light sources 124 and 140 of FIG. 43 are also configured to emit light in different directions, with the first light source 124 emitting light in a direction configured to strike the vessel 120 at an angle and the second light source 140 emitting light in a direction substantially perpendicular to a direction in which the separated fluid component is flowing through the vessel 120. In the embodiment of FIG. 44, the light received by the second light detector 138 is emitted from a position upstream of the second light detector 138, but it should be understood that the light may instead be emitted from a position downstream of the second light detector 138.

Once the optical density of the separated fluid component in the vessel 120 has been determined, it is compared to a minimum optical density value, as generally identified at 136 in FIG. 41. The minimum optical density value may represent a desirable condition of the separated fluid component in the vessel 120. For example, in the case of platelet-rich plasma, the light will have a wavelength that is absorbed or scattered by platelets, such that the optical density of the separated fluid component will be an indication of the platelet concentration of the platelet-rich plasma. The greater the concentration of platelets in the platelet-rich plasma, the higher the optical density of the platelet-rich plasma in the vessel 120 will be. The minimum optical density value may, thus, be a value corresponding to a preselected or predetermined minimum platelet concentration of the platelet-rich plasma. If the optical density of the platelet-rich plasma in the vessel 120 is less than the minimum optical density value, it is an indication that the platelet concentration of the platelet-rich plasma is too low. On the other hand, if the optical density of the platelet-rich plasma in the vessel 120 is not less than the minimum optical density value, it is an indication that the platelet concentration of the platelet-rich plasma is greater than or equal to the preselected or predetermined minimum platelet concentration.

When it has been determined that the optical density of the separated fluid component in the vessel 120 is less than the minimum optical density value, as generally identified at 142 in FIG. 41, the controller 18 may change the current target location of the interface to an optical density-adjusted target location that becomes the new current target location of the interface (replacing the initial target location or any other previously defined current target location). The optical density-adjusted target location may be anything different from the current target location of the interface, but is preferably a location that tends to remedy the condition represented by the low optical density of the separated fluid component in the vessel 120. In the case of platelet-rich plasma, the optical density-adjusted target location may be closer to the low-G wall of the centrifuge 16 or centrifugal separation chamber 36 than the current location of the interface or the current target location. Causing the interface to move from its current location toward a more radially inward position will move the red blood cells toward the first outlet 102 of the centrifugal separation chamber 36, thereby causing more platelets to exit the centrifugal separation chamber 36 in the platelet-rich plasma (i.e., increasing the platelet-collection efficiency of the system) and also increasing the optical density of the platelet-rich plasma in the vessel 120.

As described above, the position of the interface may be expressed in terms of the percentage of the ramp 106 occupied by the optically dense layer RBC, with a greater percentage equating to a position that is closer to the low-G wall of the centrifuge 16 or centrifugal separation chamber 36. Thus, in one embodiment, the optical density-adjusted target location may represent a preselected or predetermined change in the percentage of the ramp 106 currently occupied by the optically dense layer RBC. In an exemplary embodiment, the optical density-adjusted target location is determined by setting the current target location of the interface to a location corresponding to a 2% increase in the percentage of the ramp 106 occupied by the optically dense layer RBC compared to the current percentage of the ramp 106 occupied by the optically dense layer RBC. In another embodiment, the optical density-adjusted target location may represent a preselected or predetermined change in the percentage of the ramp 106 occupied by the optically dense layer RBC compared to the percentage of the ramp 106 occupied by the optically dense layer RBC at the current target location of the interface.

After adjusting the current target location of the interface based on the optical density of the separated fluid component in the vessel 120, the above-described steps may be repeated (as shown in FIG. 41) until the main wavelength of the reflected light R is not greater than the maximum wavelength value, the location of the interface is sufficiently close to the current target location of the interface or setpoint S, and the optical density of the separated fluid component in the vessel 120 is not less than the minimum optical density value. Once all of these conditions are satisfied, the controller 18 may determine to not change the current target location of the interface based on the optical density of the separated fluid component in the vessel 120 and may repeat the entire cycle to ensure that the current target location is such that the main wavelength of the reflected light R remains at or below the maximum wavelength value and the optical density of the separated fluid component in the vessel 120 remains at or above the minimum optical density value (when the interface is sufficiently close to the current target location or setpoint S to consider the optical density of the separated fluid component in the vessel 120).

The protocol of FIG. 41, in which both the color and optical density of the separated fluid component in the vessel 120 are assessed in dynamically adjusting the target interface location or setpoint S during a procedure, may be advantageous if the centrifuge outlet sensor M1 may be suitably configured. However, if the centrifuge outlet sensor M1 cannot be suitably configured (particularly, if the color of the separated fluid component in the vessel 120 cannot be assessed), it is still possible to dynamically adjust the target interface location or setpoint S during a procedure based solely on the optical density of the separated fluid component in the vessel 120. Such a protocol is illustrated in FIG. 45, while an exemplary configuration of the centrifuge outlet sensor M1 is shown in FIG. 46.

Figure 46:
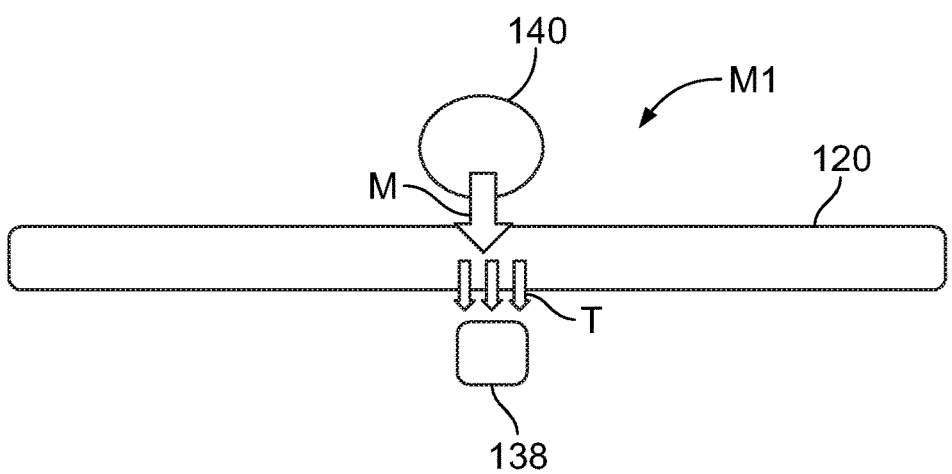
FIG. 46 is a diagrammatic view of an exemplary configuration of a centrifuge outlet sensor suitable for carrying out the protocol illustrated in FIG. 45.

The centrifuge outlet sensor M1 of FIG. 46 is comparable to the centrifuge outlet sensor M1 of FIG. 43 in that it includes a light source 140 and a light detector 138, though it omits a broadband light source 124 and a reflected light detector 126. As in the embodiment of FIG. 43, the light source 140 and the light detector 138 may be positioned directly across from each other, on opposite sides of the vessel 120. Also as in the embodiment of FIG. 43, the light source 140 may be configured to emit light M having a single wavelength suitable for determining the optical density of a separated fluid component flowing through the vessel 120. While light having a single wavelength may be sufficient to determine the optical density of the separated fluid component flowing through the vessel 120, it should be understood that the light source 140 of FIG. 46 may be configured to emit light having multiple wavelengths, including broadband light. As It should be understood that FIG. 46 illustrates one example of a centrifuge outlet sensor M1 that may be used to execute the protocol illustrated in FIG. 45 and that differently configured centrifuge outlet sensors may also be employed without departing from the scope of the present disclosure. For example, any one of the centrifuge outlet sensors shown in FIGS. 42-44 may be used to execute the protocol illustrated in FIG. 45.

Figure 45:
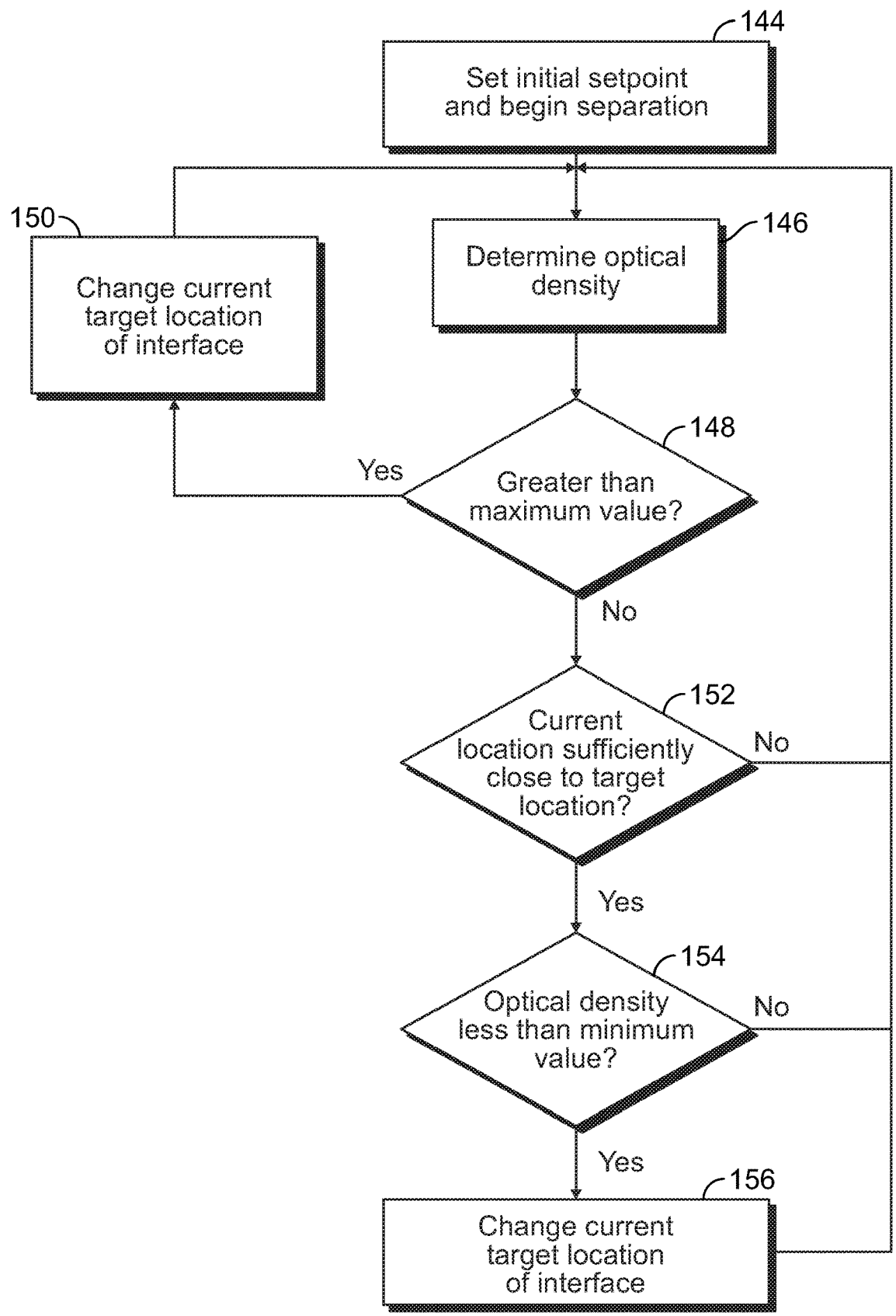
FIG. 45 illustrates an exemplary approach to mid-procedure adjustment of a target interface position based solely on the optical density of a separated fluid component.

Regardless of the particular configuration of the centrifuge outlet sensor, in the protocol of FIG. 45, a separation procedure begins with fluid being conveyed into the centrifugal separation chamber 36 of a fluid flow circuit 12 positioned within the centrifuge or centrifugal separator 16. The fluid is separated into at least two fluid components, with the separated fluid components continuously flowing through the centrifugal separation chamber 36, with an interface positioned therebetween. The separation procedure begins with an initial setpoint or target location of the interface, as generally identified at 144. This is the same as the initial step of the protocol illustrated in FIG. 41.

The separated fluid components flow out of the centrifugal separation chamber 36, with at least a portion of one of the separated fluid components eventually flowing through a vessel 120 of the fluid flow circuit 12 (FIG. 2). The separated fluid component flowing through the vessel 120 is monitored to determine its optical density, as generally identified at 146 in FIG. 45. This may be achieved by any suitable approach, including the approach described above with respect to step 134 of the protocol of FIG. 41. This optical density monitoring step is in contrast to the initial monitoring step 122 of the protocol of FIG. 41, in which the color of the separated fluid component in the vessel 120 is determined.

Once the optical density of the separated fluid component in the vessel 120 has been determined, it is compared to a maximum optical density value, as generally identified in FIG. 45 at 148. The maximum optical density value may represent an undesirable condition of the separated fluid component in the vessel 120. For example, in the case of platelet-rich plasma, as described above, the optical density of the separated fluid component in the vessel 120 will be an indication of the amount of cellular blood components in the platelet-rich plasma in the vessel 120, which may include red blood cells. The greater the amount of cellular blood components in the platelet-rich plasma, the more optically dense the platelet-rich plasma will be. The maximum optical density value may, thus, be an optical density that indicates an unacceptably high amount of red blood cells in the platelet-rich plasma. If the optical density of the platelet-rich plasma in the vessel 120 is greater than the maximum optical density value, it is an indication that too many red blood cells are being removed from the centrifugal separation chamber 36 with the platelet-rich plasma. On the other hand, if the optical density of the platelet-rich plasma in the vessel 120 is not greater than the maximum optical density value, it is an indication that the amount of red blood cells in the platelet-rich plasma is less than a preselected or predetermined amount considered to be unacceptable.

When it has been determined that the optical density of the separated fluid component in the vessel 120 is greater than the maximum optical density value, as generally identified at 150 in FIG. 45, the controller 18 may change the current target location of the interface to an upper limit-adjusted target location that becomes the new current target location of the interface (replacing the initial target location or any other previously defined current target location). The upper limit-adjusted target location may be anything different from the current target location of the interface, but is preferably a location that tends to reduce the condition represented by the elevated optical density of the separated fluid component in the vessel 120. In the case of platelet-rich plasma, the upper limit-adjusted target location may be farther from the low-G wall of the centrifuge 16 or centrifugal separation chamber 36 than the current location of the interface (not the current target location of the interface). Causing the interface to move from its current location toward a more radially outward position will move the red blood cells away from the first outlet 102 of the centrifugal separation chamber 36, thereby reducing the amount of red blood cells that will exit the centrifugal separation chamber 36 with the platelet-rich plasma and also reducing the optical density of the platelet-rich plasma in the vessel 120.

As described above, the position of the interface may be expressed in terms of the percentage of ramp 106 occupied by the optically dense layer RBC, with a greater percentage equating to a position that is closer to the low-G wall of the centrifuge 16 or centrifugal separation chamber 36. Thus, in one embodiment, the upper limit-adjusted target location may represent a preselected or predetermined change in the percentage of the ramp 106 currently occupied by the optically dense layer RBC. In an exemplary embodiment, the upper limit-adjusted target location is determined by setting the current target location of the interface to a location corresponding to a 2% reduction in the percentage of the ramp 106 occupied by the optically dense layer RBC compared to the current percentage of the ramp 106 occupied by the optically dense layer RBC. This is the same response described above with respect to the protocol of FIG. 41 when it is determined that the main wavelength of reflected light is greater than a maximum wavelength value. Detection of an elevated optical density in the protocol of FIG. 45 represents the same condition of the separated fluid component in the vessel 120 as an elevated main wavelength in FIG. 41, such that a similar response is appropriate.

After adjusting the current target location of the interface, the optical density of the separated fluid component in the vessel 120 may again be determined and compared to the maximum optical density value (as in steps 146 and 148), with the current target location of the interface again being adjusted if the optical density is still greater than the maximum optical density value. This cycle may be repeated until the optical density of the separated fluid component in the vessel 120 is not greater than the maximum optical density value, at which time the current target location of the interface is kept the same (i.e., without it being adjusted based on the optical density of separated fluid component in the vessel 120) and the controller 18 moves to the next step.

When the optical density of the separated fluid component in the vessel 120 is sufficiently low, the current interface position is compared to the current target location of the interface, as generally indicated at 152 in FIG. 45. If the position of the interface is not sufficiently close to the current target location, then the above-described steps may be repeated until the interface is at or sufficiently close to the current target location. In an exemplary embodiment (which may be the same as described above with respect to step 132 of the protocol of FIG. 41), the controller 18 determines whether the current location of the interface corresponds to the ramp 106 being occupied by a percentage of the optically dense layer RBC that is within 0.5% of the percentage of the ramp 106 occupied by the optically dense layer RBC at the current target location of the interface. As will be described in greater detail, in the next step (generally indicated at 154 in FIG. 45), the optical density of the separated fluid component in the vessel 120 is compared to a minimum optical density value. If the interface is not sufficiently close to the current target location, it is assumed that the system is not operating at the setpoint S, such that it may be premature to compare the optical density of the separated fluid component in the vessel 120 to a minimum optical density value (due to the optical density likely being too low if operating below the setpoint S and too high if operating above the setpoint S).

When it has been determined that the position of the interface is sufficiently close to the current target location or setpoint S, the optical density of the separated fluid component in the vessel 120 (as determined in step 146 of FIG. 45) is compared to a minimum optical density value, as in step 154. As in step 136 of FIG. 41, the minimum optical density value may represent a desirable condition of the separated fluid component in the vessel 120. For example, in the case of platelet-rich plasma, the optical density of the separated fluid component will be an indication of the platelet concentration of the platelet-rich plasma. The minimum optical density value may, thus, be a value corresponding to a preselected or predetermined minimum platelet concentration of the platelet-rich plasma. If the optical density of the platelet-rich plasma in the vessel 120 is less than the minimum optical density value, it is an indication that the platelet concentration of the platelet-rich plasma is too low. On the other hand, if the optical density of the platelet-rich plasma in the vessel 120 is not less than the minimum optical density value, it is an indication that the platelet concentration of the platelet-rich plasma is greater than or equal to the preselected or predetermined minimum platelet concentration.

When it has been determined that the optical density of the separated fluid component in the vessel 120 is less than the minimum optical density value, as generally identified at 156 in FIG. 45, the controller 18 may change the current target location of the interface to a lower limit-adjusted target location that becomes the new current target location of the interface (replacing the initial target location or any other previously defined current target location). The lower limit-adjusted target location may be anything different from the current target location of the interface, but is preferably a location that tends to remedy the condition represented by the low optical density of the separated fluid component in the vessel 120. In the case of platelet-rich plasma, the lower limit-adjusted target location may be closer to the low-G wall of the centrifuge 16 or centrifugal separation chamber 36 than the current location of the interface or the current target location. Causing the interface to move from its current location toward a more radially inward position will move the red blood cells toward the first outlet 102 of the centrifugal separation chamber 36, thereby causing more platelets to exit the centrifugal separation chamber 36 in the platelet-rich plasma (i.e., increasing the platelet-collection efficiency of the system) and also increasing the optical density of the platelet-rich plasma in the vessel 120.

As described above, the position of the interface may be expressed in terms of the percentage of ramp 106 occupied by the optically dense layer RBC, with a greater percentage equating to a position that is closer to the low-G wall of the centrifuge 16 or centrifugal separation chamber 36. Thus, in one embodiment, the lower limit-adjusted target location may represent a preselected or predetermined change in the percentage of the ramp 106 currently occupied by the optically dense layer RBC. In an exemplary embodiment, the lower limit-adjusted target location is determined by setting the current target location of the interface to a location corresponding to a 2% increase in the percentage of the ramp 106 occupied by the optically dense layer RBC compared to the current percentage of the ramp 106 occupied by the optically dense layer RBC. In another embodiment, the lower limit-adjusted target location may represent a preselected or predetermined change in the percentage of the ramp 106 occupied by the optically dense layer RBC at the current target location of the interface.

After adjusting the current target location of the interface based on an undesirably low optical density of the separated fluid component in the vessel 120, the above-described steps may be repeated (as shown in FIG. 45) until the optical density of the separated fluid component in the vessel 120 is not greater than the maximum optical density value, the location of the interface is sufficiently close to the current target location of the interface or setpoint S, and the optical density of the separated fluid component in the vessel 120 is not less than the minimum optical density value. Once all of these conditions are satisfied, the controller 18 may determine to not change the current target location to the lower limit-adjusted target location and may repeat the entire cycle (as shown in FIG. 45) to ensure that the current target location is such that the optical density of the separated fluid component in the vessel 120 remains at or below the maximum optical density value and (when the interface is sufficiently close to the current target location or setpoint S) at or above the minimum optical density value.

Aspects

Aspect 1. A method of adjusting a target location of an interface between separated fluid components continuously flowing through a centrifuge, comprising: separating fluid in a centrifuge into separated fluid components with an interface between the separated fluid components and with an initial target location of the interface as a current target location of the interface; removing one of the separated fluid components from the centrifuge and flowing at least a portion of said one of the separated fluid components through a vessel; exposing the vessel to light so as to cause an amount of light to be reflected by the separated fluid component in the vessel and received as a reflected light; determining a main wavelength of said reflected light; and comparing the main wavelength of said reflected light to a maximum wavelength value. Upon determining that the main wavelength of said reflected light is greater than the maximum wavelength value, the current target location of the interface is changed to a main wavelength-adjusted target location that becomes the current target location of the interface. Upon determining that the main wavelength of said reflected light is not greater than said maximum wavelength value, the current target location of the interface is not changed based on the main wavelength of said reflected light.

Aspect 2. The method of Aspect 1, further comprising, upon determining that the main wavelength of said reflected light is greater than the maximum wavelength value, repeating said determining the main wavelength of said reflected light, said comparing the main wavelength of said reflected light to said maximum wavelength value, and said changing the current target location of the interface until determining that the main wavelength of said reflected light is not greater than said maximum wavelength value.

Aspect 3. The method of any one of the preceding Aspects, wherein said changing the current target location of the interface to the main wavelength-adjusted target location includes changing the current target location to a position farther from a low-G wall of the centrifuge.

Aspect 4. The method of any one of the preceding Aspects, wherein the main wavelength-adjusted target location is a preselected or predetermined distance from the position of the interface.

Aspect 5. The method of any one of the preceding Aspects, further comprising, upon determining that the main wavelength of said reflected light is not greater than the maximum wavelength value, determining the position of the interface and comparing the position of the interface to the current target location. Upon determining that the position of the interface is not within a preselected or predetermined distance of the current target location, said determining the main wavelength of said reflected light, said comparing the main wavelength of said reflected light to said maximum wavelength value, said determining the position of the interface, and said comparing the position of the interface to the current target location are repeated until determining that the main wavelength of said reflected light is not greater than said maximum wavelength value and that the position of the interface is within said preselected or predetermined distance of the current target location.

Aspect 6. The method of Aspect 5, wherein said exposing the vessel to light also causes another amount of light to be transmitted through the separated fluid component in the vessel and received as a transmitted light, and further comprising, upon determining that the main wavelength of said reflected light is not greater than said maximum wavelength value and that the position of the interface is within said preselected or predetermined distance of the current target location, determining the optical density of the separated fluid component in the vessel based at least in part on said transmitted light and comparing the optical density of the separated fluid component in the vessel to a minimum optical density value. Upon determining that the optical density of the separated fluid component in the vessel is less than said minimum optical density value, the current target location of the interface is changed to an optical density-adjusted target location that becomes the current target location and then said determining the main wavelength of said reflected light, said comparing the main wavelength of said reflected light to said maximum wavelength value, said determining the position of the interface, said comparing the position of the interface to the current target location, said determining the optical density of the separated fluid component in the vessel, and said comparing the optical density of the separated fluid component in the vessel to said minimum optical density value are repeated until determining that the main wavelength of said reflected light is not greater than said maximum wavelength value, that the position of the interface is within said preselected or predetermined distance of the current target location, and that the optical density of the separated fluid component in the vessel is not less than said minimum optical density value. Upon determining that the optical density of the separated fluid component in the vessel is not less than said minimum optical density value, the current target location of the interface is not changed based on the optical density of the separated fluid component in the vessel.

Aspect 7. The method of Aspect 6, wherein said changing the current target location of the interface to the optical density-adjusted target location includes changing the current target location to a position closer to a low-G wall of the centrifuge.

Aspect 8. The method of any one of Aspects 6-7, wherein the optical density-adjusted target location is a preselected or predetermined distance from the position of the interface.

Aspect 9. The method of any one of Aspects 6-7, wherein the optical density-adjusted target location is a preselected or predetermined distance from the current target location of the interface.

Aspect 10. The method of any one of Aspects 6-9, wherein the fluid comprises anticoagulated whole blood, the interface is between red blood cells and platelet-rich plasma, and the separated fluid component in the vessel is platelet-rich plasma.

Aspect 11. The method of Aspect 10, wherein said comparing the main wavelength of said reflected light to said maximum wavelength value includes determining whether a preselected or predetermined amount of red blood cells is present in the platelet-rich plasma in the vessel, and said comparing the optical density of the separated fluid component in the vessel to said minimum optical density value includes determining whether the platelet-rich plasma in the vessel has at least a preselected or predetermined platelet concentration.

Aspect 12. The method of any one of the preceding Aspects, wherein said exposing the separated fluid component in the vessel to light includes emitting light from only a location positioned downstream or upstream of a location at which the reflected light is received.

Aspect 13. The method of Aspect 12, wherein said light is broadband light.

Aspect 14. The method of any one of Aspects 6-11, wherein said exposing the separated fluid component in the vessel to light includes emitting first and second lights from different locations, with a portion of the first light being received as said reflected light and a portion of the second light being received as said transmitted light.

Aspect 15. The method of Aspect 14, wherein the first and second lights are emitted in different directions.

Aspect 16. The method of any one of Aspects 14-15, wherein the first light is emitted in a direction configured to strike a surface of the vessel at an angle, and the second light is emitted in a direction substantially perpendicular to a direction in which the separated fluid component in the vessel flows through the vessel.

Aspect 17. The method of any one of Aspects 14-16, wherein the first light is broadband light and the second light has a single wavelength.

Aspect 18. The method of any one of Aspects 6-11, wherein said exposing the separated fluid component in the vessel to light includes emitting light from only a location positioned upstream or downstream of a location at which the transmitted light is received.

Aspect 19. The method of Aspect 18, wherein the light is broadband light.

Aspect 20. The method of any one of the preceding Aspects, wherein the reflected light is received at an angle with respect to a direction in which the separated fluid component in the vessel flows through the vessel.

Aspect 21. A fluid separation device, comprising: a centrifugal separator configured to receive a centrifugal separation chamber in fluid communication with a vessel; a pump system configured to convey a fluid into the centrifugal separation chamber, remove a separated fluid component from the centrifugal separation chamber, and flow at least a portion of the separated fluid component through the vessel; an interface monitoring system configured to determine the position of an interface between separated fluid components continuously flowing through the centrifugal separation chamber; a centrifuge outlet sensor configured to monitor a separated fluid component in the vessel; and a controller configured to control the pump system to convey a fluid into the centrifugal separation chamber, control the centrifugal separator to separate the fluid in the centrifugal separation chamber into separated fluid components with an interface between the separated fluid components and with an initial target location of the interface as a current target location of the interface, control the pump system to remove one of the separated fluid components from the centrifugal separation chamber and flow at least a portion of said one of the separated fluid components through the vessel, control the centrifuge outlet sensor to expose the vessel to light so as to cause an amount of light to be reflected by the separated fluid component in the vessel and received as a reflected light, determine a main wavelength of said reflected light, and compare the main wavelength of said reflected light to a maximum wavelength value. Upon determining that the main wavelength of said reflected light is greater than the maximum wavelength value, the controller changes the current target location of the interface to a main wavelength-adjusted target location that becomes the current target location of the interface. Upon determining that the main wavelength of said reflected light is not greater than said maximum wavelength value, the controller does not change the current target location of the interface based on the main wavelength of said reflected light.

Aspect 22. The fluid separation device of Aspect 21, wherein the controller is further configured to, upon determining that the main wavelength of said reflected light is greater than the maximum wavelength value, repeatedly determine the main wavelength of said reflected light, compare the main wavelength of said reflected light to said maximum wavelength value, and change the current target location of the interface until determining that the main wavelength of said reflected light is not greater than said maximum wavelength value.

Aspect 23. The fluid separation device of any one of Aspects 21-22, wherein the controller is configured to change the current target location of the interface to the main wavelength-adjusted target location by changing the current target location to a position farther from a low-G wall of the centrifugal separation chamber.

Aspect 24. The fluid separation device of any one of Aspects 21-23, wherein the main wavelength-adjusted target location is a preselected or predetermined distance from the position of the interface.

Aspect 25. The fluid separation device of any one of Aspects 21-24, wherein the controller is further configured to, upon determining that the main wavelength of said reflected light is not greater than the maximum wavelength value, determine the position of the interface and compare the position of the interface to the current target location. Upon determining that the position of the interface is not within a preselected or predetermined distance of the current target location, the controller repeatedly determines the main wavelength of said reflected light, compares the main wavelength of said reflected light to said maximum wavelength value, determines the position of the interface, and compares the position of the interface to the current target location until determining that the main wavelength of said reflected light is not greater than said maximum wavelength value and that the position of the interface is within said preselected or predetermined distance of the current target location.

Aspect 26. The fluid separation device of Aspect 25, wherein the controller is configured to control the centrifuge outlet sensor to expose the vessel to light so as to also cause another amount of light to be transmitted through the separated fluid component in the vessel and received as a transmitted light, and the controller is further configured to, upon determining that the main wavelength of said reflected light is not greater than said maximum wavelength value and that the position of the interface is within said preselected or predetermined distance of the current target location, determine the optical density of the separated fluid component in the vessel based at least in part on said transmitted light and compare the optical density of the separated fluid component in the vessel to a minimum optical density value. Upon determining that the optical density of the separated fluid component in the vessel is less than said minimum optical density value, the controller changes the current target location of the interface to an optical density-adjusted target location that becomes the current target location and then repeatedly determines the main wavelength of said reflected light, compares the main wavelength of said reflected light to said maximum wavelength value, determines the position of the interface, compares the position of the interface to the current target location, determines the optical density of the separated fluid component in the vessel, and compares the optical density of the separated fluid component in the vessel to said minimum optical density value until determining that the main wavelength of said reflected light is not greater than said maximum wavelength value, that the position of the interface is within said preselected or predetermined distance of the current target location, and that the optical density of the separated fluid component in the vessel is not less than said minimum optical density value. Upon determining that the optical density of the separated fluid component in the vessel is not less than said minimum optical density value, the controller does not change the current target location of the interface based on the optical density of the separated fluid component in the vessel.

Aspect 27. The fluid separation device of Aspect 26, wherein the controller is configured to change the current target location of the interface to the optical density-adjusted target location by changing the current target location to a position closer to a low-G wall of the centrifuge.

Aspect 28. The fluid separation device of any one of Aspects 26-27, wherein the optical density-adjusted target location is a preselected or predetermined distance from the position of the interface.

Aspect 29. The fluid separation device of any one of Aspects 26-27, wherein the optical density-adjusted target location is a preselected or predetermined distance from the current target location of the interface.

Aspect 30. The fluid separation device of any one of Aspects 26-29, wherein the fluid comprises anticoagulated whole blood, the interface is between red blood cells and platelet-rich plasma, and the separated fluid component in the vessel is platelet-rich plasma.

Aspect 31. The fluid separation device of Aspect 30, wherein the controller is configured to compare the main wavelength of said reflected light to said maximum wavelength value so as to determine whether a preselected or predetermined amount of red blood cells is present in the platelet-rich plasma in the vessel, and compare the optical density of the separated fluid component in the vessel to said minimum optical density value so as to determine whether the platelet-rich plasma in the vessel has at least a preselected or predetermined platelet concentration.

Aspect 32. The fluid separation device of any one of Aspects 21-31, wherein the centrifuge outlet sensor includes a single light source configured to emit light from only a location positioned upstream or downstream of a location at which the reflected light is received.

Aspect 33. The fluid separation device of Aspect 32, wherein said single light source is a broadband light source.

Aspect 34. The fluid separation device of any one of Aspects 26-31, wherein the centrifuge outlet sensor includes first and second light sources configured to emit first and second lights from different locations, with a portion of the first light being received as said reflected light and a portion of the second light being received as said transmitted light.

Aspect 35. The fluid separation device of Aspect 34, wherein the first and second light sources are configured to emit said first and second lights in different directions.

Aspect 36. The fluid separation device of any one of Aspects 34-35, wherein the first light source is configured to emit the first light in a direction configured to strike a surface of the vessel at an angle, and the second light source is configured to emit the second light in a direction substantially perpendicular to a direction in which the separated fluid component in the vessel flows through the vessel.

Aspect 37. The fluid separation device of any one of Aspects 34-36, wherein the first light is a broadband light and the second light has a single wavelength.

Aspect 38. The fluid separation device of any one of Aspects 26-31, wherein the centrifuge outlet sensor includes a single light source configured to emit light from only a location positioned upstream or downstream of a location at which the transmitted light is received.

Aspect 39. The fluid separation device of Aspect 38, wherein said single light source is a broadband light source.

Aspect 40. The fluid separation device of any one of Aspects 21-39, wherein the centrifuge outlet sensor includes a light detector configured to receive the reflected light at an angle with respect to a direction in which the separated fluid component in the vessel flows through the vessel.

Aspect 41. A method of adjusting a target location of an interface between separated fluid components continuously flowing through a centrifuge, comprising: separating fluid in a centrifuge into separated fluid components with an interface between the separated fluid components and with an initial target location of the interface as a current target location of the interface; removing one of the separated fluid components from the centrifuge and flowing at least a portion of said one of the separated fluid components through a vessel; exposing the vessel to light so as to cause an amount of light to be transmitted through the separated fluid component in the vessel and received as a transmitted light; determining an optical density of the separated fluid component in the vessel based at least in part on said transmitted light; and comparing the optical density of the separated fluid component in the vessel to a maximum optical density value. Upon determining that the optical density of the separated fluid component in the vessel is greater than the maximum optical density value, the current target location of the interface is changed to an upper limit-adjusted target location that becomes the current target location of the interface. Upon determining that the optical density of the separated fluid component in the vessel is not greater than said maximum optical density value, the current target location of the interface is not changed to the upper limit-adjusted target location.

Aspect 42. The method of Aspect 41, further comprising, upon determining that the optical density of the separated fluid component in the vessel is greater than the maximum optical density value, repeating said determining the optical density of the separated fluid component in the vessel, said comparing the optical density of the separated fluid component in the vessel to said maximum optical density value, and said changing the current target location of the interface until determining that the optical density of the separated fluid component in the vessel is not greater than said maximum optical density value.

Aspect 43. The method of any one of Aspects 41-42, wherein said changing the current target location of the interface to the upper limit-adjusted target location includes changing the current target location to a position farther from a low-G wall of the centrifuge.

Aspect 44. The method of any one of Aspects 41-43, wherein the upper limit-adjusted target location is a preselected or predetermined distance from the position of the interface.

Aspect 45. The method of any one of Aspects 41-44, further comprising, upon determining that the optical density of the separated fluid component in the vessel is not greater than the maximum optical density value, determining the position of the interface and comparing the position of the interface to the current target location. Upon determining that the position of the interface is not within a preselected or predetermined distance of the current target location, said determining the optical density of the separated fluid component in the vessel, said comparing the optical density of the separated fluid component in the vessel to said maximum optical density value, said determining the position of the interface, and said comparing the position of the interface to the current target location are repeated until determining that the optical density of the separated fluid component in the vessel is not greater than said maximum optical density value and that the position of the interface is within said preselected or predetermined distance of the current target location.

Aspect 46. The method of Aspect 45, further comprising, upon determining that the optical density of the separated fluid component in the vessel is not greater than said maximum optical density value and that the position of the interface is within said preselected or predetermined distance of the current target location, comparing the optical density of the separated fluid component in the vessel to a minimum optical density value. Upon determining that the optical density of the separated fluid component in the vessel is less than said minimum optical density value, the current target location of the interface is changed to a lower limit-adjusted target location that becomes the current target location and then said determining the optical density of the separated fluid component in the vessel, said comparing the optical density of the separated fluid component in the vessel to said maximum optical density value, said determining the position of the interface, said comparing the position of the interface to the current target location, and said comparing the optical density of the separated fluid component in the vessel to said minimum optical density value are repeated until determining that the optical density of the separated fluid component in the vessel is not greater than said maximum optical density value, that the position of the interface is within said preselected or predetermined distance of the current target location, and that the optical density of the separated fluid component in the vessel is not less than said minimum optical density value. Upon determining that the optical density of the separated fluid component in the vessel is not less than said minimum optical density value, the current target location of the interface is not changed to the lower limit-adjusted target location.

Aspect 47. The method of Aspect 46, wherein said changing the current target location of the interface to the lower limit-adjusted target location includes changing the current target location to a position closer to a low-G wall of the centrifuge.

Aspect 48. The method of any one of Aspects 46-47, wherein the lower limit-adjusted target location is a preselected or predetermined distance from the position of the interface.

Aspect 49. The method of any one of Aspects 46-47, wherein the lower limit-adjusted target location is a preselected or predetermined distance from the current target location of the interface.

Aspect 50. The method of any one of Aspects 46-47, wherein the fluid comprises anticoagulated whole blood, the interface is between red blood cells and platelet-rich plasma, the separated fluid component in the vessel is platelet-rich plasma, said comparing the optical density of the separated fluid component in the vessel to said maximum optical density value includes determining whether a preselected or predetermined amount of red blood cells is present in the platelet-rich plasma in the vessel, and said comparing the optical density of the separated fluid component in the vessel to said minimum optical density value includes determining whether the platelet-rich plasma in the vessel has at least a preselected or predetermined platelet concentration.

Aspect 51. A fluid separation device, comprising: a centrifugal separator configured to receive a centrifugal separation chamber in fluid communication with a vessel; a pump system configured to convey a fluid into the centrifugal separation chamber, remove a separated fluid component from the centrifugal separation chamber, and flow at least a portion of the separated fluid component through the vessel; an interface monitoring system configured to determine the position of an interface between separated fluid components continuously flowing through the centrifugal separation chamber; a centrifuge outlet sensor configured to monitor a separated fluid component in the vessel; and a controller configured to control the pump system to convey a fluid into the centrifugal separation chamber, control the centrifugal separator to separate the fluid in the centrifugal separation chamber into separated fluid components with an interface between the separated fluid components and with an initial target location of the interface as a current target location of the interface, control the pump system to remove one of the separated fluid components from the centrifugal separation chamber and flow at least a portion of said one of the separated fluid components through the vessel, control the centrifuge outlet sensor to expose the vessel to light so as to cause an amount of light to be transmitted through the separated fluid component in the vessel and received as a transmitted light, determine an optical density of the separated fluid component in the vessel, and compare the optical density of the separated fluid component in the vessel to a maximum optical density value. Upon determining that the optical density of the separated fluid component in the vessel is greater than the maximum optical density value, the controller changes the current target location of the interface to an upper limit-adjusted target location that becomes the current target location of the interface. Upon determining that the optical density of the separated fluid component in the vessel is not greater than said maximum optical density value, the controller does not change the current target location of the interface to the upper limit-adjusted target location.

Aspect 52. The fluid separation device of Aspect 51, wherein the controller is further configured to, upon determining that the optical density of the separated fluid component in the vessel is greater than the maximum optical density value, repeatedly determine the optical density of the separated fluid component in the vessel, compare the optical density of the separated fluid component in the vessel to said maximum optical density value, and change the current target location of the interface until determining that the optical density of the separated fluid component in the vessel is not greater than said maximum optical density value.

Aspect 53. The fluid separation device of any one of Aspects 51-52, wherein the controller is configured to change the current target location of the interface to the upper limit-adjusted target location by changing the current target location to a position farther from a low-G wall of the centrifugal separation chamber.

Aspect 54. The fluid separation device of any one of Aspects 51-53, wherein the upper limit-adjusted target location is a preselected or predetermined distance from the position of the interface.

Aspect 55. The fluid separation device of any one of Aspects 51-54, wherein the controller is further configured to, upon determining that the optical density of the separated fluid component in the vessel is not greater than the maximum optical density value, determine the position of the interface and compare the position of the interface to the current target location. Upon determining that the position of the interface is not within a preselected or predetermined distance of the current target location, the controller repeatedly determines the optical density of the separated fluid component in the vessel, compares the optical density of the separated fluid component in the vessel to said maximum optical density value, determines the position of the interface, and compares the position of the interface to the current target location until determining that the optical density of the separated fluid component in the vessel is not greater than said maximum optical density value and that the position of the interface is within said preselected or predetermined distance of the current target location.

Aspect 56. The fluid separation device of Aspect 55, wherein the controller is further configured to, upon determining that the optical density of the separated fluid component in the vessel is not greater than said maximum optical density value and that the position of the interface is within said preselected or predetermined distance of the current target location, compare the optical density of the separated fluid component in the vessel to a minimum optical density value. Upon determining that the optical density of the separated fluid component in the vessel is less than said minimum optical density value, the controller changes the current target location of the interface to a lower limit-adjusted target location that becomes the current target location and then repeatedly determine the optical density of the separated fluid component in the vessel, compares the optical density of the separated fluid component in the vessel to said maximum optical density value, determines the position of the interface, compares the position of the interface to the current target location, and compares the optical density of the separated fluid component in the vessel to said minimum optical density value until determining that the optical density of the separated fluid component in the vessel is not greater than said maximum optical density value, that the position of the interface is within said preselected or predetermined distance of the current target location, and that the optical density of the separated fluid component in the vessel is not less than said minimum optical density value. Upon determining that the optical density of the separated fluid component in the vessel is not less than said minimum optical density value, the controller does not change the current target location of the interface to the lower limit-adjusted target location.

Aspect 57. The fluid separation device of Aspect 56, wherein the controller is configured to change the current target location of the interface to the lower limit-adjusted target location by changing the current target location to a position closer to a low-G wall of the centrifuge.

Aspect 58. The fluid separation device of any one of Aspects 56-57, wherein the lower limit-adjusted target location is a preselected or predetermined distance from the position of the interface.

Aspect 59. The fluid separation device of any one of Aspects 56-57, wherein the lower limit-adjusted target location is a preselected or predetermined distance from the current target location of the interface.

Aspect 60. The fluid separation device of any one of Aspects 56-59, wherein the fluid comprises anticoagulated whole blood, the interface is between red blood cells and platelet-rich plasma, the separated fluid component in the vessel is platelet-rich plasma, the controller is configured to compare the optical density of the separated fluid component in the vessel to said maximum optical density value so as to determine whether a preselected or predetermined amount of red blood cells is present in the platelet-rich plasma in the vessel, and the controller is further configured to compare the optical density of the separated fluid component in the vessel to said minimum optical density value so as to determine whether the platelet-rich plasma in the vessel has at least a preselected or predetermined platelet concentration.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of adjusting a target location of an interface between separated fluid components continuously flowing through a centrifuge, comprising:
separating fluid in a centrifuge into separated fluid components with an interface between the separated fluid components and with an initial target location of the interface as a current target location of the interface;
removing one of the separated fluid components from the centrifuge and flowing at least a portion of said one of the separated fluid components through a vessel;
exposing the vessel to light so as to cause an amount of light to be transmitted through the separated fluid component in the vessel and received as a transmitted light;
determining an optical density of the separated fluid component in the vessel based at least in part on said transmitted light; and
comparing the optical density of the separated fluid component in the vessel to a maximum optical density value, wherein
upon determining that the optical density of the separated fluid component in the vessel is greater than the maximum optical density value, changing the current target location of the interface to an upper limit-adjusted target location that becomes the current target location of the interface, and
upon determining that the optical density of the separated fluid component in the vessel is not greater than said maximum optical density value, not changing the current target location of the interface to the upper limit-adjusted target location.

2. The method of claim 1, further comprising, upon determining that the optical density of the separated fluid component in the vessel is greater than the maximum optical density value, repeating said determining the optical density of the separated fluid component in the vessel, said comparing the optical density of the separated fluid component in the vessel to said maximum optical density value, and said changing the current target location of the interface until determining that the optical density of the separated fluid component in the vessel is not greater than said maximum optical density value.

3. The method of claim 1, wherein said changing the current target location of the interface to the upper limit-adjusted target location includes changing the current target location to a position farther from a low-G wall of the centrifuge.

4. The method of claim 1, wherein the upper limit-adjusted target location is a preselected or predetermined distance from the position of the interface.

5. The method of claim 1, further comprising
upon determining that the optical density of the separated fluid component in the vessel is not greater than the maximum optical density value, determining the position of the interface and comparing the position of the interface to the current target location, and
upon determining that the position of the interface is not within a preselected or predetermined distance of the current target location, repeating said determining the optical density of the separated fluid component in the vessel, said comparing the optical density of the separated fluid component in the vessel to said maximum optical density value, said determining the position of the interface, and said comparing the position of the interface to the current target location until determining that the optical density of the separated fluid component in the vessel is not greater than said maximum optical density value and that the position of the interface is within said preselected or predetermined distance of the current target location.

6. The method of claim 5, further comprising
upon determining that the optical density of the separated fluid component in the vessel is not greater than said maximum optical density value and that the position of the interface is within said preselected or predetermined distance of the current target location, comparing the optical density of the separated fluid component in the vessel to a minimum optical density value, wherein
upon determining that the optical density of the separated fluid component in the vessel is less than said minimum optical density value, changing the current target location of the interface to a lower limit-adjusted target location that becomes the current target location and then repeating said determining the optical density of the separated fluid component in the vessel, said comparing the optical density of the separated fluid component in the vessel to said maximum optical density value, said determining the position of the interface, said comparing the position of the interface to the current target location, and said comparing the optical density of the separated fluid component in the vessel to said minimum optical density value until determining that the optical density of the separated fluid component in the vessel is not greater than said maximum optical density value, that the position of the interface is within said preselected or predetermined distance of the current target location, and that the optical density of the separated fluid component in the vessel is not less than said minimum optical density value, and
upon determining that the optical density of the separated fluid component in the vessel is not less than said minimum optical density value, not changing the current target location of the interface to the lower limit-adjusted target location.

7. The method of claim 6, wherein said changing the current target location of the interface to the lower limit-adjusted target location includes changing the current target location to a position closer to a low-G wall of the centrifuge.

8. The method of claim 6, wherein the lower limit-adjusted target location is a preselected or predetermined distance from the position of the interface.

9. The method of claim 6, wherein the lower limit-adjusted target location is a preselected or predetermined distance from the current target location of the interface.

10. The method of claim 6, wherein
the fluid comprises anticoagulated whole blood,
the interface is between red blood cells and platelet-rich plasma,
the separated fluid component in the vessel is platelet-rich plasma,
said comparing the optical density of the separated fluid component in the vessel to said maximum optical density value includes determining whether a preselected or predetermined amount of red blood cells is present in the platelet-rich plasma in the vessel, and said comparing the optical density of the separated fluid component in the vessel to said minimum optical density value includes determining whether the platelet-rich plasma in the vessel has at least a preselected or predetermined platelet concentration.

11. A fluid separation device, comprising:
a centrifugal separator configured to receive a centrifugal separation chamber in fluid communication with a vessel;
a pump system configured to convey a fluid into the centrifugal separation chamber, remove a separated fluid component from the centrifugal separation chamber, and flow at least a portion of the separated fluid component through the vessel;
an interface monitoring system configured to determine the position of an interface between separated fluid components continuously flowing through the centrifugal separation chamber;
a centrifuge outlet sensor configured to monitor a separated fluid component in the vessel; and
a controller configured to
control the pump system to convey a fluid into the centrifugal separation chamber,
control the centrifugal separator to separate the fluid in the centrifugal separation chamber into separated fluid components with an interface between the separated fluid components and with an initial target location of the interface as a current target location of the interface,
control the pump system to remove one of the separated fluid components from the centrifugal separation chamber and flow at least a portion of said one of the separated fluid components through the vessel,
control the centrifuge outlet sensor to expose the vessel to light so as to cause an amount of light to be transmitted through the separated fluid component in the vessel and received as a transmitted light,
determine an optical density of the separated fluid component in the vessel, and
compare the optical density of the separated fluid component in the vessel to a maximum optical density value, wherein
upon determining that the optical density of the separated fluid component in the vessel is greater than the maximum optical density value, change the current target location of the interface to an upper limit-adjusted target location that becomes the current target location of the interface, and
upon determining that the optical density of the separated fluid component in the vessel is not greater than said maximum optical density value, not change the current target location of the interface to the upper limit-adjusted target location.

12. The fluid separation device of claim 11, wherein the controller is further configured to, upon determining that the optical density of the separated fluid component in the vessel is greater than the maximum optical density value, repeatedly determine the optical density of the separated fluid component in the vessel, compare the optical density of the separated fluid component in the vessel to said maximum optical density value, and change the current target location of the interface until determining that the optical density of the separated fluid component in the vessel is not greater than said maximum optical density value.

13. The fluid separation device of claim 11, wherein the controller is configured to change the current target location of the interface to the upper limit-adjusted target location by changing the current target location to a position farther from a low-G wall of the centrifugal separation chamber.

14. The fluid separation device of claim 11, wherein the upper limit-adjusted target location is a preselected or predetermined distance from the position of the interface.

15. The fluid separation device of claim 11, wherein the controller is further configured to
upon determining that the optical density of the separated fluid component in the vessel is not greater than the maximum optical density value, determine the position of the interface and compare the position of the interface to the current target location, and
upon determining that the position of the interface is not within a preselected or predetermined distance of the current target location, repeatedly determine the optical density of the separated fluid component in the vessel, compare the optical density of the separated fluid component in the vessel to said maximum optical density value, determine the position of the interface, and compare the position of the interface to the current target location until determining that the optical density of the separated fluid component in the vessel is not greater than said maximum optical density value and that the position of the interface is within said preselected or predetermined distance of the current target location.

16. The fluid separation device of claim 15, wherein the controller is further configured to
upon determining that the optical density of the separated fluid component in the vessel is not greater than said maximum optical density value and that the position of the interface is within said preselected or predetermined distance of the current target location, compare the optical density of the separated fluid component in the vessel to a minimum optical density value, wherein
upon determining that the optical density of the separated fluid component in the vessel is less than said minimum optical density value, change the current target location of the interface to a lower limit-adjusted target location that becomes the current target location and then repeatedly determine the optical density of the separated fluid component in the vessel, compare the optical density of the separated fluid component in the vessel to said maximum optical density value, determine the position of the interface, compare the position of the interface to the current target location, and compare the optical density of the separated fluid component in the vessel to said minimum optical density value until determining that the optical density of the separated fluid component in the vessel is not greater than said maximum optical density value, that the position of the interface is within said preselected or predetermined distance of the current target location, and that the optical density of the separated fluid component in the vessel is not less than said minimum optical density value, and
upon determining that the optical density of the separated fluid component in the vessel is not less than said minimum optical density value, not change the current target location of the interface to the lower limit-adjusted target location.

17. The fluid separation device of claim 16, wherein the controller is configured to change the current target location of the interface to the lower limit-adjusted target location by changing the current target location to a position closer to a low-G wall of the centrifuge.

18. The fluid separation device of claim 16, wherein the lower limit-adjusted target location is a preselected or predetermined distance from the position of the interface.

19. The fluid separation device of claim 16, wherein the lower limit-adjusted target location is a preselected or predetermined distance from the current target location of the interface.

20. The fluid separation device of claim 16, wherein
the fluid comprises anticoagulated whole blood,
the interface is between red blood cells and platelet-rich plasma,
the separated fluid component in the vessel is platelet-rich plasma,
the controller is configured to compare the optical density of the separated fluid component in the vessel to said maximum optical density value so as to determine whether a preselected or predetermined amount of red blood cells is present in the platelet-rich plasma in the vessel, and
the controller is further configured to compare the optical density of the separated fluid component in the vessel to said minimum optical density value so as to determine whether the platelet-rich plasma in the vessel has at least a preselected or predetermined platelet concentration.

* * * * *